US008374837B2

(12) United States Patent
De Winter et al.

(10) Patent No.: US 8,374,837 B2
(45) Date of Patent: Feb. 12, 2013

(54) DESCRIPTORS OF THREE-DIMENSIONAL OBJECTS, USES THEREOF AND A METHOD TO GENERATE THE SAME

(75) Inventors: Hans Louis Jos De Winter, Schilde (BE); Wilfried Gert Roger Langenaeker, Kortessem (BE)

(73) Assignee: Silicos NV, Diepenbeek (BE)

( * ) Notice: Subject to any disclaimer, the term of this patent is extended or adjusted under 35 U.S.C. 154(b) by 1065 days.

(21) Appl. No.: 12/155,413

(22) Filed: Jun. 4, 2008

(65) Prior Publication Data
US 2009/0306950 A1 Dec. 10, 2009

(51) Int. Cl.
*G06F 19/00* (2006.01)
(52) U.S. Cl. ............................................ 703/11; 702/19
(58) Field of Classification Search .................... 703/11; 702/19
See application file for complete search history.

(56) References Cited

U.S. PATENT DOCUMENTS
5,025,388 A 6/1991 Cramer, III et al.

FOREIGN PATENT DOCUMENTS
EP 1 862 927 A1 12/2007
WO WO 2004/023349 3/2004

OTHER PUBLICATIONS

Search Report of the International Searching Authority in International Patent Application No. PCT/EP2008/056821, Sep. 4, 2008.
Sadowski et al , "From Atoms and Bonds to Three-Dimensional Atomic Coordinates: Automatic Model Builders", Chem. Rev. 7, 1993, pp. 2567-2581.
Bostrom et al., "Assessing the Performance of OMEGA With Respect to Retrieving Bioactive Conformations", J. Mol. Graph. Mod. 21, 2003, pp. 449-462.
Bultinck et al., "The Electronegativity Equalization Method II: Applicability of Different Atomic Charge Schemes", J Phys. Chem A 106, 2002, pp. 7895-7901.
Bultinck et al., "Fast Calculation of Quantum Chemical Molecular Descriptors from the Electronegativity Equalization Method", J. Chem. Inf Comput Sci. 43, 2003, pp. 422-428.
Heiden et al., "A New Approach to Analysis and Display of Local Lipophilicity/Hydrophilicity Mapped on Molecular Surfaces", J. Comput. Aided Mol. Des. 7, 1993, pp. 503-514.
Mannhold et al . Comparative Evaluation of the Predictive Power of Calculation Procedures for Molecular Lipophilicity, J Pharm. Sci. 84, 1995, pp. 1410-1419.
Gaillard et al , "Molecular Lipophilicity Potential, a tool in 3D QSAR: Method and applications". J. Comput Aided Mol Des 8, 1994, pp. 83-96.
Ertl et al , "Fast Calculation of Molecular Polar Surface Area as a Sum of Fragment-Based Contributions and Its Application to the Prediction of Drug Transport Properties", J Med. Chem 43, 2000, pp. 3714-3717.
Rey et al , "Development of Molecular Hydrogen-bonding Potentials (MHBPs) and Their Application to Structure-Permeation Relations", J. Mol. Graph. Model. 19, 2001, pp. 521-535.
Kier and Hall, "An Electrotopological-State Index for Atoms in Molecules", Pharm. Res 7, 1990, pp. 801-807.

(Continued)

*Primary Examiner* — Michael Borin
(74) *Attorney, Agent, or Firm* — Bacon & Thomas, PLLC

(57) ABSTRACT

A computer-based method of generating a descriptor of a three-dimensional object wherein the following steps are performed for each of a set of one or more cages and for each of one or more properties:
(i) enclosing entirely the three-dimensional object in the cage,
(ii) for each property, while keeping the three-dimensional object entirely enclosed in the cage by varying one or more dimensions of the cage, minimizing the interaction value resulting from the interaction between the three dimensional object and the cage by changing the relative orientation between the three-dimensional object and the cage, and
(iii) assigning each of the obtained minimized interaction values to a distinct position in the descriptor.

17 Claims, 12 Drawing Sheets

OTHER PUBLICATIONS

Hall and Kier, "Electrotopological State Indices for Atom Types: A Novel Combination of Electronic, Topological, and Valence State Information", J Chem. Inf. Comput Sci. 35, 1995, pp. 1039-1045.

Vinter and Trollope. "Multiconformational Composite Molecular Potential Fields in the Analysis of Drug Action I. Methodology and First Evaluation Using 5-HT and Histamine Action as Examples", J Comput-Aided Mol. Des. 9, 1995, pp. 297-307.

Mestres et al , "A Molecular Field-Based Similarity Approach to Pharmacophoric Pattern Recognition". J. Mol. Graph. Model. 15, 1997, pp. 114-121.

Laskowski, Roman A , "SURFNET: A Program for Visualizing Molecular Surfaces, Cavities, and Intermolecular Interactions", J. Mol. Graph. 13. 1995, pp. 323-330.

Richards, Frederic M., "Areas, Volumes. Packing, and Protein Structure". Ann Rev. Biophys Bioeng 6. 1977. pp. 151-176.

Sandberg et al , "New Chemical Descriptors Relevant for the Design of Biologically Active Peptides. A Multivariate Characterization of 87 Amino Acids", J. Med. Chem 41. 1998. pp. 2481-2491.

Bayly et al , "A Well-Behaved Electrostatic Potential Based Method Using Charge Restraints for Deriving Atomic Charges: The RESP Model", J. Phys. Chem 97, 1993. pp. 10269-10280.

McElroy et al., "QSAR and Classification of Murine and Human Soluble Epoxide Hydrolase Inhibition by Urea-Like Compounds". J. Med. Chem. 46, 2003, pp. 1066-1080.

Rose et al., "Modeling Blood-Brain Barrier Partitioning Using the Electrotopological State", J.Chem. Inf. Comput Sci 42, 2002. pp. 651-666.

Clark, David E., "Rapid Calculation of Polar Molecular Surface Area and Its Application to the Prediction of Transport Phenomena 2. Prediction of Blood-Brain Barrier Penetration". J Pharm Sci , vol. 88, No. 8, Aug. 1999, pp. 815-821.

DESCRIPTORS OF THREE-DIMENSIONAL OBJECTS, USES THEREOF AND A METHOD TO GENERATE THE SAME

FIELD OF INVENTION

The invention relates to the field of molecular modelling for drug discovery and to the application of virtual screening algorithms for chemical discovery and in particular to the use of computer based systems. In particular, a method is disclosed to generate descriptors, e.g. to transform any type of three-dimensional objects with associated properties, such as molecular species with their associated atomic properties, into strings of real numbers. Once obtained, these descriptors can be used to understand and derive structure/activity relationships, virtual screening of molecular databases, and virtual synthesis of molecules with predefined properties as well as lead to synthesis of such compounds. In addition to its application on small molecules, the method can also be applied to the binding pockets of proteins or other biomolecules, e.g. by converting this pocket into its mirror image.

BACKGROUND OF THE INVENTION

Traditionally, the design of novel molecular species (e.g. drugs) has essentially been a trial-and-error process despite the tremendous efforts devoted to it by pharmaceutical and academic research groups. In an attempt to counter the rapidly increasing costs associated with the discovery of new medicines, new computer-based approaches are conducted. Modern approaches to computer-aided molecular design fall into two general categories. The first includes structure-based methods which utilise the three-dimensional structure of a ligand-bound receptor. The second approach includes ligand-based methods in which the physicochemical or structural properties of ligand molecular species are characterized. A classic example of this concept is a quantitative structure-activity relationship (QSAR) model. Quantitative structure-activity relationships are mathematical relationships linking chemical structures—represented in the form of molecular descriptors—and pharmacological activity in a quantitative manner for a series of molecular species.

Virtual screening is the computational process whereby libraries of existing or virtual molecular species are searched for molecular species that meet well-defined criteria. In general, virtual screening is applied to search for molecular species that might be active against certain disease related proteins, whereas the activity is derived from the calculated interaction between the protein and the molecular species. Scoring of the molecular species is performed using well-defined mathematical functions with the aim to prioritize these molecular species for further analysis. Typically, two major virtual screening tendencies can be distinguished.

The first tendency consists of the protein structure-based approach whereby the potential binding pocket of a protein is used as reference function. The selection of potential binding pockets is still a major challenge within the pharmaceutical industry. Once the reference function is known, one can start with the screening of molecular species having the desired properties with respect to binding to the target protein. A number of suitable methods have been described:

Docking of molecular species within the target protein.
Pharmacophore representation of the binding pocket of the target protein.

The second tendency consists of a ligand-based approach whereby molecular species with known affinity for a target protein or disease model are used as reference function. A model is derived from these reference molecular species and can be used to annotate other molecular species with respect to their potential binding capabilities. A number of suitable ligand-based approaches have been described. Some are two-dimensional and some are three-dimensional. The 2D methods have the advantage of being applied very efficiently to search molecular databases. The disadvantage is that they are rather unspecific, which is not the case for the somewhat slower 3D methods. These forms of virtual screening can be integrated with available high-throughput screening (HTS) results. Below is provided an overview of a typical ligand-based virtual screening application which is combined with high-throughput screening:

1. Select a training set of molecular species from the HTS results;
2. Train a model based on common characteristics of the selected molecular species;
3. Use the model to score the other molecular species within the database;
4. Validate the prioritized molecular species using the HTS results or by means of new biochemical assay data;
5. Repeat the procedure until convergence of the model has been reached.

Such modern high-throughput screening platforms requires the implementation and integration of efficient and robust virtual screening protocols and algorithms.

In order to be suitable for use within a computational context, molecular information must be translated into a suitable form, generally called a descriptor. Molecular descriptors can vary greatly in their complexity. A simple example may be a structural key descriptor, which takes the form of a binary indicator variable that encodes the presence of certain substructure or functional features. Other descriptors, such as HOMO (Highest Occupied Molecular Orbital) and LUMO (Lowest Unoccupied Molecular Orbital) energies, require semi-empirical or quantum mechanical calculations and are therefore more time-consuming to compute. Molecular descriptors are often categorised according to their dimensionality, which refers to the structural representation from which the descriptor values are derived. In general, one can classify the current molecular descriptors as one dimensional (1D), two dimensional (2D), or three dimensional (3D).

One dimensional descriptors are a reflection of the 'bulk' properties of molecular species, like the molecular weight, the number of atoms, or the molecular distribution between hydrophilic and lipophilic phases. One dimensional descriptors are generally fast to calculate and can be calculated from the molecular composition alone. Nevertheless, one dimensional descriptors lack any information about the molecular connectivity between the atoms, and are therefore rather of limited accuracy when applied to drug discovery and virtual screening problems.

The calculation of two dimensional descriptors requires knowledge of the molecular topology, and comprises information on the presence or absence of well-defined functional moieties, topological distances between well-defined atoms, and information regarding sidechains and ringsystems. Two dimensional descriptors have found their use in chemical similarity analyses and structure-activity relationships, and are useful in complementing three dimensional descriptors. The most widely used two-dimensional descriptors are molecular fingerprints, 'E-state' indices, and hologram QSAR descriptors.

Molecular fingerprints are essentially bitmaps consisting of on- and offbits, where each position along the bitmap is assigned to a specific and well-defined molecular fragment. If that particular fragment exists in the molecular species under consideration, then the corresponding bit is set to on, otherwise it is left as off. There are two general methods of 2D fingerprint generation. The first, known as the 'hashed' method, uses a set of rules for generating the fragments for fingerprinting. The second method, known as the 'keyed' method, requires a priori substructural definitions for all fragments that should be searched for during the fingerprint generation process. Similarity assessments between molecular species based on two dimensional fingerprints can be done in a number of ways, although the most commonly used metrics are based on Tanimoto coefficients. The Tanimoto coefficient compares the number of fingerprint bits in common between pairs of structures.

Electrotopological state (E-state) indices capture both molecular connectivity and the electronic character of a molecular species. The method makes use of the hydrogen-suppressed graph to represent the molecular structure. The focus of the method is on the individual atoms and hydride groups of the molecular skeleton. Intrinsic valence and sigma electron descriptors are assigned to each atom depending on the counts of valence and sigma electrons of the corresponding atoms. From these atom descriptors molecular connectivity indices may be calculated by multiplying the sigma and valence values for each atom in a fragment within a molecular species. This product is then converted to the reciprocal square root and called the connectivity subgraph term.

Hologram QSAR (HQSAR) is another two dimensional descriptor approach in which counts are made of the number of times each fragment is encountered in a molecular species, rather than merely using bitmaps to represent the absence or presence of particular fragments. The resulting integer strings are subsequently hashed to reduce string length and used as input for Partial Least Squares analysis to correlate with biological data.

Three-dimensional descriptors are a reflection of the molecular shape and of the spacial arrangements of the functional moieties which are thought to be important for the interaction between ligand and receptor. As implied by the name, three-dimensional descriptors are generated from a three dimensional representation of molecular species. With very few exceptions, the descriptor values are computed from a static conformation, which is either a standard conformation with ideal geometries generated from programs such as CORINA (Sadowski et al., 1993, *Chem. Rev.* 7, 2567-2581) or Omega (Boström et al., 2003, *J. Mol. Graph. Mod.* 21, 449-462), or a conformation that is fitted against a target X-ray structure or a pharmacophore.

An example of three-dimensional descriptor is described in U.S. Pat. No. 5,025,388, which relates to the CoMFA methodology. The CoMFA methodology, which is an acronym for Comparative Molecular Field Analysis, is a 3D quantitative structure-activity relationship technique which ultimately allows one to design and predict activities of molecular species. The database of molecular species with known properties, the training set, are suitably aligned in 3D space according to various methodologies. Charges are then calculated for each molecular species at a level of theory deemed appropriate. Steric and electrostatic fields are subsequently calculated for each molecular species by interaction with a probe atom at a series of grid points surrounding the aligned database in three-dimensional space. Finally, correlation of these field energy terms with a property of interest is performed by means of partial least squares with cross-validation, giving a measure of the predictive power of the model.

The CoMFA method has the inconvenience that it requires the alignment of the molecules of investigation in the same reference frame, which makes the applicability of CoMFA to molecular systems of different structural classes difficult. It also has the inconvenience not to permit the discrimination between stereoisomers, additionally, the descriptors obtained by this method only translate the electronic properties of the molecular species. There is therefore a need in the art for an improved, stereospecific and fast method of generating descriptors from three-dimensional objects by translating a wider range of their properties. There is also a need in the art for such a method not requiring alignment of the molecules under investigation.

SUMMARY

The present invention has the object to provide methods and apparatus for molecular modelling, e.g. methods to characterise (and optionally) cluster three-dimensional objects based on their interaction with a spatial, physicochemical environment of which the interaction with the object can be calculated and characterized in that said spatial, physicochemical environment consists of at least one cage comprising a set of points on its surface, thus defining a geometrical and three-dimensional arrangement of a number of points, surrounding the three-dimensional object, thereby forming a set of interaction points to mimick a spatial of physicochemical environment of which the interaction with the three-dimensional object can be calculated, hereinafter also referred to as an 'artificial' cage surrounding the three-dimensional object. Said methods find their application in amongst others drug discovery, virtual screening, molecular discovery and in particular in the use of computer based systems to characterize and cluster molecular entities, e.g. in compound libraries, molecular databases, QSAR model building, ligand- and protein-based drug design.

The invention results from the unexpected finding that pairs of three-dimensional objects that interact in a similar way with a set of these cages, are also interacting in a similar way with their natural environment, which could be expressed as, for example, the binding affinity to protein receptors, or the penetration through the blood-brain barrier.

When applied to molecules, a process in accordance with the present invention involves a number of steps. The first step is the generation of the three dimensional coordinates of the molecule and the calculation or assignment of properties to at least some and preferably each of the atoms. Secondly, a set of cages is generated which are then used, in the third and final phase, to evaluate the interaction of the molecules with each of the cages. Each of the obtained interaction values is stored as a separate descriptor interaction value $V_i$. Pairs of descriptors can then be compared by means of a suitable distance measure, for instance, simple Euclidean distance calculations. The method may make use of a computer or a computing system. In the case of molecular species, the method is based on the evaluation, in an automated fashion, of the interaction of molecular species with an artificial environment implemented as a set of cages surrounding the molecular species.

Accordingly, the methods of the present invention include;
a method and system to transform any three dimensional objects, in particular molecular species, generally represented by a set of atomic coordinates in three-dimensional space, and the associated properties of these atoms as represented by real or integer numbers, into one dimensional strings of real numbers.
a method and system to create a spatial, physicochemical environment of which the interaction with the object can be calculated and that consists of at least one cage comprising a set of points on its surface, thus defining a geometrical and three-dimensional arrangement of a number of 'interaction' points, surrounding the three-dimensional object, and wherein each of these interaction points are given one or more property value that is relevant to calculate a physically or a physicochemical interaction value between the three-dimensional object and its environment.

A method and system to determine minimized interaction value between the three-dimensional object and said spatial, physicochemical environment.

When applied to molecules, the present invention should speed up the process of drug design, discovery, and identification by allowing researchers to characterise molecules with respect to their potential of interacting with their environment, being for example protein active sites, aquatic environment, or biological membranes. Applications of the invention can be found in virtual screening and QSAR model building, ligand- and protein-based drug design, and molecular database clustering and characterisation.

A further object of the present invention is the use of the aforementioned methods to understand and derive structure/activity relationships, virtual screening of molecular databases, and virtual synthesis of molecules with predefined properties as well as to lead to synthesis of such compounds. In an even further objective, the methods and apparatus can be used for investigating the binding to pockets of proteins or other biomolecules such as molecules or substances that have an antigenic determinant.

For any of the embodiments of the present invention a step may be included of synthesizing a molecule based on the molecular modeling according to the present invention.

In embodiments, the present invention relates to a method of generating a descriptor of a three-dimensional object represented by a set of coordinates, said descriptor being a string of interaction values $V_i$ of one or more properties, represented by value Vb, at chosen coordinates within said set of coordinates of said three-dimensional object, with one or more properties, represented by value Vc, of the interaction points of a cage surrounding said three-dimensional object said method comprising the steps of:

(i) enclosing entirely said three-dimensional object in said cage,
(ii) for each property, while keeping said three-dimensional object entirely enclosed in said cage by varying one or more dimensions of said cage, minimizing the interaction value Vi resulting from the interaction between said three dimensional object and said cage by changing the relative orientation between the three-dimensional object and said cage, and
(iii) assigning each of the obtained minimized interaction values $V_i$ to a distinct position in said descriptor.

For instance, the methods of the present invention may relate to computer-based methods of generating a descriptor of a three dimensional object, and the three dimensional object is being selected from the group consisting of (i) a surface obtained from a biomolecule pocket (e.g. obtained by a method comprising the steps of (a) filling said biomolecule pocket with a set of one or more spheres, and (b) generating a surface around said set of one or more spheres), (ii) a three-dimensional configuration of a molecular species, or (iii) a catalytic surface, said three-dimensional object being represented by a set of coordinates. In particular, the three-dimensional object is a molecular species.

The properties used in the methods of the present invention, are in particular atomic properties such as for example shape index, partial atomic charges, lypophilicity, softness, hardness, electrophilicity. For each of the different possible properties, the absolute value of each Vc (interaction points) should be related to the absolute values of Vb, (coordinates, i.e. points within the three-dimensional object) in order to be able to calculate a physically meaningful interaction value between each cage point and the molecular entity. For all cages surrounding the molecular entity, the absolute values of Vc should be consistent and on the same magnitude scale. In order to limit the number of possible Vc combinations, a number of discrete values can be selected. For instance, Vc can be selected from +1, 0, or −1, as another example Vc can be selected from +1 and −1, the sum of all the property values of a cage can be either zero or non-zero.

In an alternative embodiment, the method of generating a descriptor of a three-dimensional object represented by a set of coordinates, said descriptor being a string of interaction values $V_i$, comprises the steps of:

(i) enclosing entirely said three-dimensional configuration of said molecular species in said cage in such a way that said three-dimensional object is at a fixed distance from said cage or within a maximum distance of said cage,
(ii) for each property, while keeping said three-dimensional configuration of a molecular species entirely enclosed in said cage in such a way that said three-dimensional object is at said fixed distance from said cage or within said maximum distance from said cage by adapting one or more dimensions of said cage, minimizing (or maximizing or averaging) the interaction value $V_i$ resulting from the interaction between said chosen coordinates of said three-dimensional object and said points of said cage by sampling over the entire rotational space the relative orientation between said three-dimensional object and said cage, and
(iii) assigning each of the obtained minimized interaction values $V_i$ to a distinct position in said descriptor.

The present invention also provides a computer-based system for generating a descriptor of a three-dimensional object represented by a set of coordinates, said descriptor being a string of interaction values $V_i$, the system comprising:

(i) means for loading one or more properties and a value $V_b$ having been attributed for each of said one or more properties at chosen coordinates within the set of coordinates representing said three-dimensional object;
(ii) means for loading representation of a set of one or more cages enclosing entirely said three-dimensional object, said one or more cages having each a three-dimensional shape on the surface of which a set of points are positioned, one or more properties (i.e. the same one or more properties as attributed to said three-dimensional object) and a value $V_c$ for each of said one or more properties being attributed to each of said points,
(iii) means for minimizing the interaction value $V_i$ resulting from the interaction between said three dimensional object and said cage by changing the relative orientation between the three-dimensional object and said cage for each property by varying one or more dimensions of said cage, while keeping said three-dimensional object entirely enclosed in said cage, and
(iv) Means for assigning each of the obtained minimized interaction values $V_i$ to a distinct position in said descriptor.

The present invention also provides a computer-based system for generating a descriptor of a three-dimensional object represented by a set of coordinates, said descriptor being a string of values, the system comprising:

means for loading representations of one or more cages having each a three-dimensional shape and a volume $V_v$, and
means for performing for each of a set of one or more cages including:

(i) Means for enclosing entirely said three-dimensional object in said cage,
(ii) Means for optimizing the relative orientation between said three-dimensional object and said cage and for varying one or more dimensions of said cage so as to minimize the volume $V_v$ of said cage while keeping said three-dimensional object entirely enclosed in said cage, and
(iii) Means for assigning each of said minimized volume $V_v$ to a distinct position in said descriptor.

The present invention also provides a system for generating a three-dimensional quantitative structure activity relationship (3D-QSAR) of a series of molecular species, the system comprising:
a) Means for loading a three dimensional configuration for each of said molecular species,
b) Means for generating a descriptor in accordance with the present invention, said descriptor being a string of interaction values, for each three-dimensional configuration,
c) Means for associating each of said descriptors to a measured biological activity,
d) Means for defining a plurality of equations, each equation corresponding to one molecular species of the series, wherein in each equation said measured biological activity of the corresponding molecular species is set equal to a weighted linear combination of said interaction values, said weighted linear combination being weighted by unknown coefficients, said plurality of equations forming a system of equations, and
e) Means for finding an at least approximate solution to the system of equations, said solution being the set of coefficients which come closest to making each equation true.

For any of the apparatus embodiments of the present, apparatus may be included for synthesizing a molecule based on the molecular modeling according to the present invention.

The present invention includes computer program products such as software for implementing any of the methods of the invention. For example, the present invention also includes a machine-readable data or signal carrier storing an executable program which implements any of the methods of the present invention when executed on a computing device. Such a data carrier may be a magnetic storage device such as a diskette, hard driven magnetic tape or an optical data carrier such as a DVD or CD-ROM, solid state memory such as a USB memory stick, flash memory, etc.

DEFINITIONS

Figure 1:
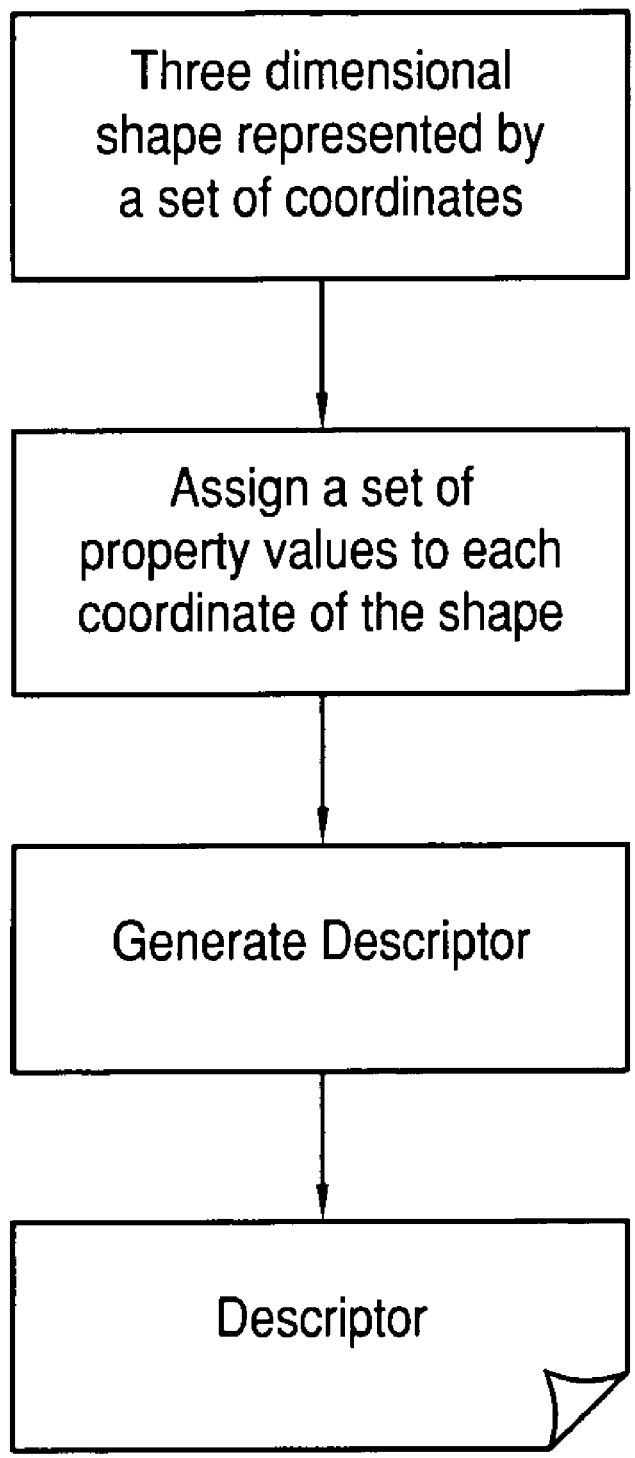
FIG. 1 is a flowchart showing a process of the generation of descriptors according to an embodiment of the present invention.

As used herein and unless stated otherwise, the terms "molecular species" refers to molecules of any size including macromolecules and polymers. It refers as well to inorganic molecules, organic molecules including biomolecules such as biopolymers that include proteins and polynucleic acids. It further refers to any assembly of molecules such as supramolecules, supermolecules and the like.

DETAILED DESCRIPTION OF THE INVENTION

The present invention will be described with reference to certain drawings and to certain embodiments but this description is by way of example only. In a first embodiment, the present invention relates to a computer-based method of generating a descriptor, i.e. a string of interaction values $V_i$, of a three-dimensional object represented by a set of coordinates with an 'artificial' cage surrounding said object and represented by a set of interaction points. The method comprises the steps of attributing one or more properties and a value $V_b$ for each of these one or more properties at chosen coordinates within the set of coordinates of the three-dimensional object, and of attributing one or more properties and a value $V_c$ (i.e. the same one or more properties as attributed to said three-dimensional object) for each of these one or more properties at interaction points of the cage. Subsequently, the following steps are performed for each of a set of one or more cages:
(i) enclosing entirely the three-dimensional object in a cage,
(ii) for each property, while keeping the three-dimensional object entirely enclosed in the cage by varying one or more dimensions of the cage, minimizing the interaction value $V_i$ resulting from the interaction between the three dimensional object (e.g. chosen atomic positions of the three-dimensional configuration of a molecular species) and the cage (i.e. the points of the cage) by changing the relative orientation between the three-dimensional object and the cage (e.g. by sampling over the entire rotational space), and
(iii) assigning each of the obtained minimized interaction values $V_i$ to a distinct position in the descriptor.

In other words, in this first embodiment, the present invention relates to a computer based method of generating a descriptor of a three-dimensional object represented by a set of coordinates, said descriptor being a string of interaction values $V_i$, said method comprising the step of attributing one or more properties and a value $V_b$ for each of said one or more properties at chosen coordinates within said set of coordinates of said three-dimensional object, characterized in that the following steps are performed for each of a set of one or more cages (said set of one or more cage implementing an artificial environment), said one or more cages having each a three-dimensional shape on the surface of which a set of points are positioned, one or more properties (the same one or more properties as attributed to said three-dimensional object) and a value $V_c$ for each of said one or more properties being attributed to each of said points:

(i) enclosing entirely said three-dimensional object in said cage,
(ii) for each property, while keeping said three-dimensional object entirely enclosed in said cage by varying one or more dimensions of said cage, minimizing (or maximizing or averaging) the interaction value $V_i$ resulting from the interaction between said three dimensional object (i.e. said chosen coordinates of said three dimensional object) and said cage (i.e. said points of said cage) by changing (e.g. sampling over the entire rotational space) the relative orientation between the three-dimensional object and said cage, and
(iii) assigning each of the obtained minimized (or maximized or averaged) interaction values $V_i$ to a distinct position in said descriptor As an optional feature, the value $V_c$ attributed to each of the points positioned on each cage is limited to only a few values e.g. either +1, 0 or −1, preferably +1 or −1. This feature has the advantage to permits fast computation. This also enables more easily the sum of the values $V_c$ for each cage to be zero, which is another optional feature of the present invention having the advantage to simulate a realistic globally neutral environment Although there are no particular requirements as to the dimension of the cage, the distance between the interaction points and the three-dimensional object is preferably such that a meaningful interaction value between at least some and preferably each cage point and the molecular entity can be calculated. In a particular embodiment, the distance between the interaction points and the molecular entity should be such that at least one of the property value spheres of the interaction points and the molecular entity are in reach of one another. In an even further embodiment, for the minimizing of the interaction value $V_i$, the dimensions of the cage are selected so that at least two positions on the object are closer, i.e. not farther away than 1 nm to the cage, preferably 0.3 nm to the cage. This feature is advantageous because it permits to calculate the descriptors of the present invention in a standardized and reproducible way.

As another optional feature, the set of points positioned on each cage comprises between four and twelve points. This is advantageous because a higher number of points would reduce the calculation speed without improving substantially the fidelity of the translation of the structure and properties of the three-dimensional object into the descriptor.

As another optional feature, at least one of the cages is stereospecific. This is advantageous because it permits to produce descriptors which keep information about the stereospecificity of the molecular species from which it is derived.

As another optional feature, the one or more cages are selected from cuboid cages on the surface of which said set of points are one of:
a) four points occupying half of the corners of each face of said cuboid cage, or
b) six points occupying the center of each face of said cuboid cage, or
c) eight points occupying all corners of said cuboid cage, or
d) twelve points occupying the middle of each edge of said cuboid cage.

Those type of cages and points distributions are advantageous because of their symmetry and their simplicity. This permits faster computational processes.

As another optional feature, the one or more cages are four or more cages. This is advantageous because the use of four or more cages improves significantly the fidelity with which the descriptor translates the structure and the properties of the three-dimensional object.

As another optional feature, each value $V_b$ is normalized before to perform step (ii). This is advantageous because normalization of the $V_b$ values improves significantly the fidelity with which small differences in the property distributions of the three-dimensional object are reflected in the calculated interaction values $V_i$.

As an optional feature of the first embodiment, one or more cage shapes are used (e.g. cuboid and ellipsoid) and a value $V_v$ is calculated for one cage of each cage shape (e.g. a $V_v$ is calculated for a cuboid cage and another $V_v$ is calculated for an ellipsoid cage), wherein for one cage of each cage shape, $V_v$ is calculated by:
(i) enclosing entirely the three-dimensional object in said cage,
(ii) optimizing the relative orientation between the three-dimensional object and the cage and varying one or more dimensions of the cage so as to minimize the volume $V_v$ of the cage while keeping the three-dimensional object entirely enclosed in the cage.

Once minimized, $V_v$ can be assigned as an interaction value at a distinct position in the descriptor.

A second embodiment of the present invention relates to a computer-based method of generating a descriptor, i.e. a string of interaction values, of a three-dimensional object represented by a set of coordinates. In this method, the following steps are performed for each of a set of one or more cages having each a three-dimensional shape and a volume $V_v$,
(i) enclosing entirely the three-dimensional object in a cage,
(ii) optimizing the relative orientation between the three-dimensional object and the cage and varying one or more dimensions of the cage so as to minimize the volume $V_v$ of the cage while keeping the three-dimensional object entirely enclosed in the cage, and
(iii) assigning each of the minimized volume $V_v$ as an interaction value at a distinct position in the descriptor.

This embodiment has the advantage to permit the generation of descriptors from objects characterized only by their shape.

As an optional feature, at least one of the one or more cages used in the first or the second embodiment of the present invention is a cuboid. This is advantageous because cuboid cages lead to faster calculation and to descriptors translating with good fidelity the three-dimensional shape and the properties of the three-dimensional objects they describe.

As another optional feature, the three-dimensional object of the first or the second embodiment of the present invention is a three-dimensional configuration of a molecular species (which can be determined either via a computer simulation, via one or more laboratory analysis means or via a combination of computer simulation and one or more laboratory analysis means) and the chosen coordinates are chosen atomic positions. This is advantageous since many applications of the use of descriptors are in the field of molecular sciences such as biology or chemistry.

As another optional feature, the chosen atomic positions of the three-dimensional configuration of the molecular species of the first or second embodiment of the present invention are all the atomic positions of the three-dimensional configuration of the molecular species. This is advantageous because it permits to translate into a descriptor the three-dimensional structure and the properties of the molecular species with the highest fidelity.

As another optional feature, the conformation of the three-dimensional configuration of the molecular species is varied after step (i) and before step (iii) of either the first or the second embodiment of the present invention so as to minimize, in the case of the first embodiment of the present invention, the calculated interaction value $V_i$ resulting from the interaction between the three-dimensional configuration of the molecular species and the cage or so as to minimize in the case of the second embodiment of the present invention the volume $V_v$ of the cage while keeping the three-dimensional object entirely enclosed in the cage. This is advantageous because it permits to increase the reproducibility of the descriptor obtained.

As another optional feature of the present invention, the three-dimensional object is a surface obtained from a biomolecule pocket, e.g. from a protein or from the glycosylation of a protein or from any substance with an antigenic determinant, by a method comprising the steps of:
a) filling the biomolecule, e.g. protein, pocket with a set of one or more spheres, and
b) generating a surface around this set of one or more spheres.

The translation of a biomolecule, e.g. protein pocket, such as e.g. an active site into a descriptor according to an embodiment of the present invention is advantageous because it permits to classify those biomolecule, e.g. protein pockets according to the physicochemical properties of their active sites, or to evaluate ligand binding by evaluating the similarity between the respective descriptors of both the ligand and the biomolecule, e.g. protein pocket.

A third embodiment of the present invention relates to the assessing of the similarity between a reference three-dimensional object and a test three-dimensional object by calculating the similarity between the corresponding descriptors generated according to any embodiment of the present invention.

A fourth embodiment of the present invention relates to a method of generating a three-dimensional quantitative structure activity relationship (3D-QSAR) of a series of molecular species comprising the steps of:
a) obtaining a three dimensional configuration for each of the molecular species,
b) generating a descriptor, i.e. a string of interaction values, for each three-dimensional configurations according to any embodiment of the present invention,
c) associating each of these descriptor to a measured biological, e.g. therapeutic, activity,
d) defining a plurality of equations, each equation corresponding to one molecular species of the series, wherein in each equation the measured biological activity of the corresponding molecular species is set equal to a weighted linear combination of the interaction values, the weighted linear combination being weighted by unknown coefficients and the plurality of equations forming a system of equations, and
e) finding an at least approximate solution to the system of equations, the solution being the set of coefficients which come closest to making each equation true.

In an embodiment, the present invention relates to a computer-based method of generating a descriptor of a three-dimensional object. The descriptor of the present invention has been given the name Spectrophore™. The present invention includes several different types of descriptor, e.g. "protein descriptor" or "ligand descriptor". Three-dimensional objects which can be represented by a descriptor according to the present invention are any kind of three-dimensional objects that can be represented by a set of coordinates. Although the nature of the three-dimensional object is not critical for the present invention, the present invention is particularly useful when applied to objects that are interesting to compare to each other (e.g. because they have an activity at least partly related to their structure or for any other reason). Typical although non-limitative examples are solid surfaces (such as but not limited to catalytic surfaces), molecular species (such as but not limited to biologically active molecular species or catalytic molecular species) or interior surfaces of protein pockets among others. In the rest of the present description, the present invention will be described mainly with reference to objects which are biologically active molecular species but it will be well understood to the person skilled in the art that the present invention can be applied to any three-dimensional objects that can be represented by a set of coordinates.

The descriptor generated by the method of the present invention is represented as a string of interaction values $V_i$ of the form $(V_{i1}, V_{i2}, \ldots V_{in})$ with interaction values $V_{i1}$ to $V_{in}$ being all real numbers. The total number of points in the descriptor (NS) is calculated from the number of atomic properties (NP) and the number of cages (NC) (Equation 1):

$$NS = NP \times NC \quad \text{(Equation 1)}$$

The order occupied by the different interaction values $V_i$ within the descriptor is not a limiting feature of the present invention. Any order can be used. An example of order is a grouping of the interaction values $V_i$ within the descriptor by property type, followed by cage type. The following table illustrates this for a descriptor according to the present invention calculated using three properties and four different cages (the length of the descriptor in this example is 3×4=12 interaction values):

|  | Descriptor position | | | | | | | | | | | |
| --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 |
| Cage | 1 | 2 | 3 | 4 | 1 | 2 | 3 | 4 | 1 | 2 | 3 | 4 |
| Property | 1 | 1 | 1 | 1 | 2 | 2 | 2 | 2 | 3 | 3 | 3 | 3 |

The position of each interaction value within the descriptor can be calculated from Equation 2:

$$n = c + ((p-1) \times NC) \quad \text{(Equation 2)}$$

with n the position of the interaction value calculated from the c'th cage and the p'th atomic property, and NC the total number of cages.

Alternatively, c and p can be deduced from the position n using Equations 3 and 4:

$$p = 1 + \text{floor}\left(\frac{n-1}{NC}\right) \quad \text{(Equation 3)}$$

$$c = n - \left(NC \times \text{floor}\left(\frac{n-1}{NC}\right)\right) \quad \text{(Equation 4)}$$

with $$\text{floor}\left(\frac{n-1}{NC}\right)$$

in Equations 3 and 4 being a function returning the largest integer value that is less than or equal to $$\left(\frac{n-1}{NC}\right).$$

In an embodiment of the present invention, the descriptor of the three-dimensional object is generated by a computer-based method including the following steps:

When the three-dimensional object is a molecular species, the first step is to determine a three-dimensional configuration and a set of coordinates, i.e. a set of atomic positions for this molecular species via a computer simulation, one or more laboratory analysis means or via a combination of computer simulation and one or more laboratory analysis means. For instance, the molecular conformations can be generated by using programs such as but not limited to CORINA or Omega, derived experimentally by using methods such as but not limited to X-ray, infra-red spectroscopy (IR) or nuclear magnetic resonance (NMR) techniques or modelled according to a pharmacophoric pattern (i.e. a three-dimensional distribution of chemical functional groups or classes which are thought to be responsible for a specific pharmacological activity) or hypothesis.

The second step consists in the generation and the attribution of one or more properties and a value $V_b$ for each of these properties at chosen positions on the surface of the three-dimensional object. When the three-dimensional object is a molecular species, the chosen positions are atomic positions of the set of atomic positions determined in the first step of the method. Preferably, the chosen atomic positions are all the atomic positions of the molecular species. The nature of the property is not a limiting feature of the present invention and any kind of property can be used. Examples of properties usable in the present invention include but are not limited to: optical properties (such as but not limited to color, absorption, transmission, index of refraction, scattering, luminescence intensity or color and the likes), mechanical properties (such as but not limited to pressure, hardness (e.g. micro-hardness), and the likes), electrical properties (e.g. conductivity), magnetical properties (e.g. magnetic susceptibility), thermal properties (e.g. temperature), shape indices and the likes. Shape indices can be generated by calculating, for each chosen position, the position's deviation from the average radius of the three-dimensional object. This can be performed in the following way:

1. Determining the three-dimensional object centre of geometry (COG);
2. Calculating the distance between each position and the three-dimensional object COG;
3. Calculating the average radius of the three-dimensional object by averaging all the three-dimensional object distances (determined in step 2);
4. Calculating the differences between the average radius of the three-dimensional object (as calculated in step 3) and the distance of each position to the COG (as calculated in step 2);
5. Normalising the values obtained in step 4 by dividing with the average radius of the three-dimensional object (as calculated in step 3). This is the shape index.

In the case when the three-dimensional object is a molecular species, suitable properties includes atomic properties such as but not limited to atomic partial charges, atomic lipophilicities, atomic softnesses, atomic hardnesses, electrophilicities, atomic shape indices and the likes. Those properties can be calculated in many ways. The exact origin of the calculation method is not critical for the present invention. For instance, atomic partial charges, softnesses, hardnesses, and electrophilicities can be calculated by using an EEM-based approach, as described by Bultinck et al. (2002, *J. Phys. Chem. A*. 106, 7895-7901; 2003, *J. Chem. Inf. Comput. Sci.* 43, 422-428). Atomic lipophilicities can be calculated and assigned using a rule-based method as described by many research groups (see e.g. Heiden et al., 1993, *J. Comput. Aided Mol. Des.* 7, 503-514; Mannhold et al., 1995, *J. Pharm. Sci.* 84, 1410-1419; Gaillard et al., 1994, *J. Comput. Aided Mol. Des.* 8, 83-96). Atomic shape indices can be generated in a similar way as described above for shape indices by calculating, for each atom, the atom's deviation from the average molecular radius. This can be performed in the following way:

1. Determining the molecular centre of geometry (COG);
2. Calculating the distance between each atom and the molecular COG;
3. Calculating the average molecular radius by averaging all the atomic distances (determined in step 2);
4. Calculating the differences between the average molecular radius (as calculated in step 3) and the distance of each atom to the COG (as calculated in step 2);
5. Normalising the values obtained in step 4 by dividing with the average molecular radius (as calculated in step 3). This is the atomic shape index.

The presented list of properties should not be considered as being exhaustive. Any property (e.g. atomic property) might be used as input to calculate descriptors. Other examples of such properties include topological polar surface areas (Ertl et al., 2000, *J. Med. Chem.* 43, 3714-3717), hydrogen bonding potentials (Rey et al., 2001, *J. Mol. Graph. Model.* 19, 521-535), 'E-state'-indices (Kier & Hall, 1990, *Pharm. Res.* 7, 801-807 and Hall & Kier, 1995, *J. Chem. Inf. Comput. Sci.* 35, 1039-1045), number of connected atoms or connected bonds, among others.

Figure 4:
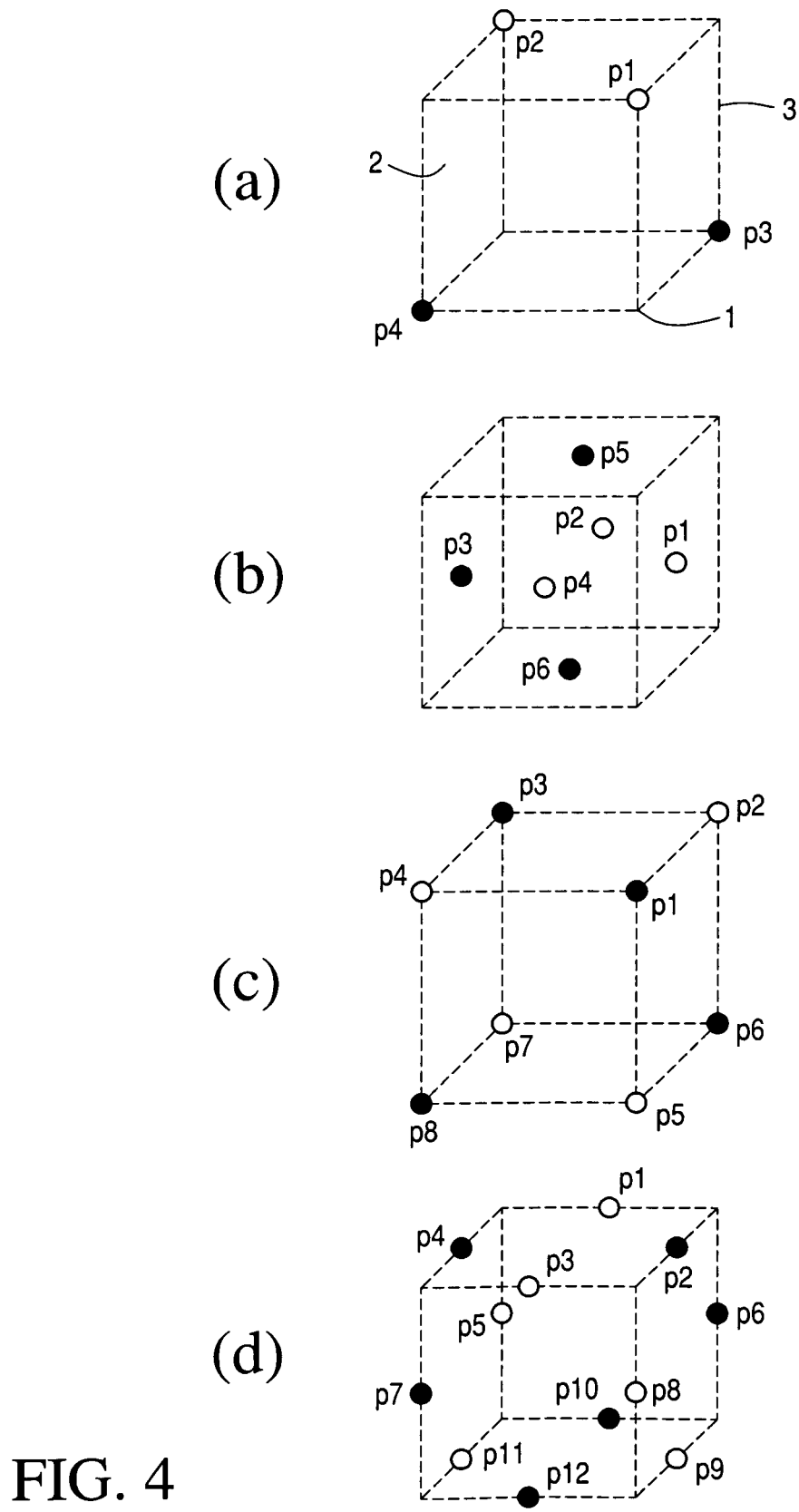
FIG. 4 shows four examples of cages with their corresponding spatial distribution of property values $V_c$ according to an embodiment of the present invention.

The third step consists in enclosing entirely the three-dimensional object (e.g. the molecular species) in a first cage of a set of one or more cages. The number of cages can be any number above or equal to one, preferably above or equal to four. These cages have a three-dimensional shape. As used herein and unless provided otherwise, the term "cage" relates to a geometrical three-dimensional shape on which a number of points are preferably arranged. A "cage" is used for surrounding a three-dimensional object, such as a three-dimensional representation of a molecular entity, from which a descriptor is to be generated. During the determination of an interaction value $V_i$ of said descriptor, the distance between the cage and the three-dimensional object is kept small by varying one or more dimensions of the cage. Although the dimension of the cage can be varied along the three spatial axis, a cuboid cage will remain a cuboid cage, an ellipsoid cage will remain an ellipsoid cage and so on. For instance, a maximum value or a fixed value can be set for the distance between the cage and the three-dimensional object. Preferably, a fixed value is set. Once this value is set, the coordinates of the cage are adapted in such a way as to enclose the three-dimensional object entirely and as to have the cage at or within said set distance of the three-dimensional object before each $V_i$ calculation. This maximum or fixed value can for instance be 1 nm or preferably 0.3 nm (e.g. scaled on the three-dimensional object that served as a model to form its three-dimensional representation, e.g. scaled on the molecular species when the three dimensional object is a representation of a molecular species). The exact method used to adapt the distance between the three-dimensional object and the cage is not crucial. In an embodiment of the present invention, the distance between the three-dimensional object and the cage can be adapted as follow: first, a reference system such as for instance a set of three mutually perpendicular axis (x, y and z) is created in a simulated three-dimensional space. Second, the three dimensional object is placed in the three-dimensional space. This can for instance be done in such a way that the geometrical center of the three-dimensional object coincide with the intersection of the three axes x, y and z (i.e. at the point (0,0,0)). Third, the geometric center of the cage is also placed at the point (0,0,0). In the case of cuboid cages, each face of the cage is preferably parallel to two axis of the reference system. At this stage, the dimensions of the cage can be adapted either before or after a first rotational step of the three-dimensional object in order to (1) enclose completely said object, and (2) for the distance between the cage and the object to reach the set fixed value (or in another embodiment, to reach a value inferior or equal to the set maximum value). The adaptation of the dimensions of the cage can for instance be performed as follow: First, the cage is linearly deformed along a first axis of the reference system (e.g. the x-axis). In the case of a cuboid cage, this has for effect to change the distance between the two parallel faces of the cuboid being perpendicular to this first axis. This deformation is such that the distance between a first of said two parallel faces and the coordinate (e.g. the atom) of the three-dimensional object having the lower x component is inferior to said maximum value (or is equal to said fixed value) and that said coordinate is enclosed in the cage. This deformation is also such that the distance between the other of said two parallel faces and the coordinate (e.g. the atom) of the three-dimensional object having the higher x component is inferior or equal to said maximum value (or, in another embodiment, is equal to said fixed value) and that said coordinate is enclosed in the cage. Similarly, the cage can then be linearly deformed along the two remaining axis of the reference system. After that the shape of the cage has been adapted to the three-dimensional object, the interaction between the points of the cage (with their values $V_c$) and the chosen positions of the object (with their values $V_b$) is calculated in order to generate a first interaction value $V_i$. Then, the three-dimensional object is rotated along its centre of geometry, the shape of the cage is adapted as previously and a second interaction value $V_i$ is calculated. This process is repeated until the whole rotational space has been scanned. At this point in time, the smallest (or the biggest, or the averaged) $V_i$ value calculated between the cage and the three-dimensional object is recorded as one element of the descriptor. Another cage (or another property) is then selected which will lead to a second element of the descriptor. This process is continued until an interaction value has been determined of all cage-property couples. The distance between the cage and the three-dimensional object (e.g. a molecular entity) is preferably kept constant along all three spatial dimensions. The distance may be different for each of the axis, but is kept constant upon a change in the relative orientation between the molecular entity and the representation points. In other words, a change in the orientation of the molecular entity in the reference system (e.g. along the three dimensional axes of the coordinate frame) will lead to changes in the cage size in order to keep the distance between the cage and the three-dimensional object (e.g. a molecular entity) constant. In a particular embodiment and in order to determine a representative physicochemical interaction value between the molecular entity and its environment, the distance between the interaction points and the molecular entity is such that at least one of the interaction points has its property value interaction sphere (i.e. a sphere defined by a radius around the point above which the interaction with positions of the three-dimensional object would becomes negligible) overlapping with the property value interaction sphere of a chosen position of the three-dimensional object. In some embodiments, this distance between the three-dimensional object and the cage can be said to be at said set maximum or fixed value when each face of said cage is at said fixed value of at least on eof the chosen positions of the three-dimensional object. The cage with its points serve to mimic a physicochemical environment with which the three-dimensional object interact and wherein this interaction can be calculated. Each of these points are given one or more property values $V_c$ that are relevant to calculate one or more physical or a physicochemical interaction values $V_i$ between the three-dimensional object (e.g. three dimensional representation of a molecular entity) and its environment (the cage). The calculated value of such interaction is dependent on the spatial arrangement of the different points of the cage, the three-dimensional shape of the three-dimensional object (e.g. a molecular entity, a catalytic surface or the interior surface of a protein pocket), and the relative orientation between the three-dimensional object (e.g. a molecular entity) and the different points of the cage. The three-dimensional shape of each cage can be any shape such as but not limited to polyhedra (such as but not limited to pyramids (e.g. tetrahedron), polygonal prisms (e.g. cuboids), polygonal antiprisms, and the likes), ellipsoids (e.g. sphere), cones, and the likes including truncated versions thereof. A typical example of three-dimensional shape of a cage that can be used in the present invention is a cuboid cage. On the surface of this shape, a set of points are positioned. One or more properties and values $V_c$ for each of said one or more properties are attributed to each of these points. These properties must be the same as the properties attributed to the chosen positions of the three-dimensional objects so that an interaction $V_i$ can be calculated between the points of a cage and the chosen positions of the three-dimensional object. For instance, if a property A and a property B are attributed to chosen position of a three-dimensional object, the same properties A and B are attributed to the point of the cage so that for each cage, a $V_i$ can be calculated for property A and a $V_i$ can be calculated for property B. For each of the different possible cages and properties, the absolute value of each $V_c$ is preferably selected in such a way as to be in the same order of magnitude as the absolute values of $V_b$, in order to be more easily able to calculate a physically meaningful interaction value between each cage point and the three-dimensional object (e.g. a molecular entity). For each cage surrounding the molecular entity, the absolute values of $V_c$ are preferably on the same degree of magnitude. $V_c$ are either reals or integers and can be either positive numbers or negative numbers. In order to limit the number of possible $V_c$ combinations, a number of discrete values can be selected. For instance, $V_c$ can be selected from +1, 0 or −1. As another example, $V_c$ can be selected between +1 and −1. The sum of all the property values of a cage can be either zero or non zero. Preferably, it is zero. The number of points (i.e. the number of points per cage) can be any number equal or superior to four, preferably between four and twelve. A very large number of spatial arrangements of the points on the surface of the cages are possible. FIG. 4 illustrates examples of spatial arrangement according to a particular embodiment of the present invention, in the case of a cuboid cage.

At the top of FIG. 4, a cuboid cage (a) is displayed. Four points marked p1 to p4 occupy half of the corners (1) of each face (2) of the cuboid cage (a) (quadrupole). Directly below cage (a), a cuboid cage (b) is displayed. Six points marked p1 to p6 occupy the center of each face (2) of the cuboid cage (b) (hexapole). Directly below cage (b), a cuboid cage (c) is displayed eight points marked p1 to p8 occupy all corners (1) of the cuboid cage (c) (octapole). At the bottom of FIG. 4, a cuboid cage (d) is displayed. Twelve points marked p1 to p12 occupy the middle of each edge (3) of the cuboid cage (d) (dodecapole). The table presented below shows a series of 58 cages when for instance four different arrangements (quadrupole, hexapole, octapole and dodecapole as defined in FIG. 4) and two property values (+1 and −1) are used.

| Type | Property value $V_c$ at position | | | | | | | | | | | | Stereo-specific? |
|---|---|---|---|---|---|---|---|---|---|---|---|---|---|
| | 1 | 2 | 3 | 4 | 5 | 6 | 7 | 8 | 9 | 10 | 11 | 12 | |
| Quadrupole | +1 | +1 | −1 | −1 | | | | | | | | | No |
| Hexapole | +1 | +1 | +1 | −1 | −1 | −1 | | | | | | | No |
| Hexapole | +1 | +1 | −1 | −1 | +1 | −1 | | | | | | | No |
| Octapole | +1 | −1 | +1 | −1 | −1 | +1 | −1 | +1 | | | | | No |
| Octapole | +1 | −1 | +1 | +1 | −1 | −1 | −1 | +1 | | | | | No |
| Octapole | +1 | +1 | −1 | −1 | −1 | −1 | +1 | +1 | | | | | No |
| Octapole | +1 | −1 | −1 | +1 | +1 | −1 | +1 | −1 | | | | | No |
| Octapole | −1 | +1 | +1 | +1 | +1 | −1 | −1 | −1 | | | | | No |
| Octapole | +1 | −1 | +1 | +1 | −1 | −1 | +1 | −1 | | | | | Yes |
| Octapole | +1 | −1 | −1 | +1 | −1 | −1 | +1 | +1 | | | | | Yes |
| Dodecapole | +1 | +1 | −1 | −1 | −1 | +1 | +1 | −1 | −1 | −1 | +1 | +1 | No |
| Dodecapole | +1 | +1 | −1 | −1 | +1 | −1 | +1 | −1 | −1 | −1 | +1 | +1 | No |
| Dodecapole | +1 | +1 | +1 | −1 | −1 | −1 | −1 | −1 | −1 | +1 | +1 | +1 | No |
| Dodecapole | +1 | +1 | +1 | −1 | −1 | −1 | −1 | +1 | +1 | −1 | +1 | +1 | No |
| Dodecapole | +1 | +1 | +1 | −1 | −1 | +1 | −1 | +1 | −1 | −1 | +1 | −1 | No |
| Dodecapole | +1 | +1 | +1 | −1 | +1 | −1 | +1 | −1 | −1 | +1 | −1 | −1 | No |
| Dodecapole | +1 | +1 | +1 | −1 | −1 | +1 | −1 | −1 | −1 | +1 | −1 | −1 | No |
| Dodecapole | +1 | +1 | +1 | +1 | −1 | −1 | −1 | −1 | +1 | −1 | +1 | −1 | No |
| Dodecapole | +1 | +1 | +1 | +1 | −1 | −1 | +1 | −1 | +1 | −1 | −1 | −1 | No |
| Dodecapole | +1 | +1 | +1 | +1 | −1 | +1 | −1 | −1 | −1 | −1 | −1 | −1 | No |
| Dodecapole | +1 | +1 | +1 | +1 | +1 | −1 | −1 | −1 | −1 | −1 | −1 | −1 | No |
| Dodecapole | +1 | +1 | −1 | −1 | −1 | +1 | −1 | −1 | +1 | +1 | −1 | +1 | No |
| Dodecapole | +1 | +1 | −1 | −1 | −1 | +1 | +1 | +1 | −1 | +1 | −1 | −1 | Yes |
| Dodecapole | +1 | +1 | +1 | −1 | −1 | −1 | −1 | +1 | −1 | +1 | +1 | −1 | Yes |
| Dodecapole | +1 | +1 | +1 | −1 | −1 | −1 | +1 | −1 | −1 | +1 | +1 | −1 | Yes |
| Dodecapole | +1 | +1 | +1 | −1 | −1 | −1 | +1 | −1 | −1 | +1 | −1 | +1 | Yes |
| Dodecapole | +1 | +1 | +1 | −1 | −1 | −1 | +1 | −1 | −1 | +1 | +1 | −1 | Yes |
| Dodecapole | +1 | +1 | +1 | −1 | −1 | −1 | +1 | −1 | +1 | +1 | −1 | −1 | Yes |
| Dodecapole | +1 | +1 | +1 | −1 | −1 | −1 | +1 | −1 | +1 | −1 | +1 | −1 | Yes |
| Dodecapole | +1 | +1 | +1 | −1 | −1 | −1 | +1 | +1 | −1 | −1 | −1 | −1 | Yes |
| Dodecapole | +1 | +1 | +1 | −1 | −1 | −1 | +1 | +1 | +1 | −1 | −1 | −1 | Yes |
| Dodecapole | +1 | +1 | +1 | −1 | −1 | +1 | +1 | −1 | −1 | −1 | −1 | +1 | Yes |
| Dodecapole | +1 | +1 | +1 | −1 | −1 | +1 | −1 | −1 | −1 | +1 | +1 | −1 | Yes |
| Dodecapole | +1 | +1 | +1 | −1 | −1 | +1 | +1 | −1 | −1 | +1 | −1 | −1 | Yes |
| Dodecapole | +1 | +1 | +1 | −1 | −1 | +1 | +1 | −1 | −1 | −1 | +1 | −1 | Yes |
| Dodecapole | +1 | +1 | +1 | −1 | +1 | −1 | −1 | +1 | +1 | −1 | −1 | −1 | Yes |
| Dodecapole | +1 | +1 | +1 | +1 | −1 | −1 | −1 | −1 | −1 | −1 | +1 | +1 | Yes |
| Dodecapole | +1 | +1 | +1 | +1 | −1 | −1 | −1 | −1 | −1 | +1 | +1 | −1 | Yes |
| Dodecapole | +1 | +1 | −1 | −1 | +1 | −1 | +1 | −1 | +1 | −1 | −1 | +1 | Yes |
| Dodecapole | +1 | +1 | +1 | −1 | −1 | −1 | −1 | −1 | +1 | +1 | +1 | −1 | Yes |
| Dodecapole | +1 | +1 | +1 | −1 | −1 | +1 | −1 | −1 | −1 | −1 | +1 | +1 | Yes |
| Dodecapole | +1 | +1 | +1 | −1 | +1 | −1 | −1 | −1 | −1 | +1 | −1 | +1 | Yes |
| Dodecapole | +1 | +1 | +1 | −1 | +1 | −1 | −1 | −1 | −1 | +1 | +1 | +1 | Yes |
| Dodecapole | +1 | +1 | +1 | −1 | +1 | −1 | −1 | −1 | +1 | −1 | −1 | +1 | Yes |
| Dodecapole | +1 | +1 | +1 | −1 | +1 | −1 | −1 | −1 | +1 | −1 | +1 | −1 | Yes |
| Dodecapole | +1 | +1 | +1 | −1 | +1 | +1 | −1 | −1 | −1 | −1 | −1 | +1 | Yes |
| Dodecapole | +1 | +1 | +1 | −1 | +1 | −1 | +1 | −1 | +1 | −1 | −1 | −1 | Yes |
| Dodecapole | +1 | +1 | +1 | −1 | +1 | −1 | +1 | −1 | −1 | +1 | −1 | −1 | Yes |
| Dodecapole | +1 | +1 | +1 | −1 | +1 | −1 | +1 | −1 | −1 | −1 | −1 | +1 | Yes |
| Dodecapole | +1 | +1 | +1 | −1 | +1 | −1 | +1 | −1 | −1 | −1 | +1 | −1 | Yes |
| Dodecapole | +1 | +1 | +1 | −1 | +1 | +1 | −1 | −1 | −1 | −1 | +1 | −1 | Yes |
| Dodecapole | +1 | +1 | +1 | −1 | +1 | +1 | −1 | −1 | +1 | −1 | −1 | −1 | Yes |
| Dodecapole | +1 | +1 | +1 | −1 | +1 | +1 | −1 | −1 | −1 | +1 | −1 | −1 | Yes |
| Dodecapole | +1 | +1 | +1 | +1 | −1 | −1 | +1 | −1 | −1 | +1 | −1 | −1 | Yes |
| Dodecapole | +1 | +1 | +1 | +1 | +1 | −1 | −1 | −1 | −1 | +1 | −1 | −1 | Yes |
| Dodecapole | +1 | +1 | +1 | +1 | +1 | −1 | −1 | −1 | −1 | −1 | +1 | −1 | Yes |
| Dodecapole | +1 | +1 | +1 | +1 | +1 | −1 | −1 | −1 | −1 | +1 | −1 | −1 | Yes |

Depending on the values $V_c$ attributed to each of those points, some of these spatial arrangements are stereo specific (i.e. there is a difference between the stereo specific cage and its mirror image), while other arrangements are non-stereo specific. The position and the orientation of the cage are generated in such a way that the cage encloses the three-dimensional object (e.g. the molecular species) entirely. In the example of the cages in the table hereabove, which are all cuboid cages, a number of constraint can be imposed.

A first possibility is to consider the x-, y-, and z-edges of the cuboid frame (i.e. the frame of the cuboid cage) as being independent of each other, and are defined by the x-, y-, and z-extents of the three dimensional object (e.g. of the molecular species). For instance, if the extent along the x-axis of the three-dimensional object is from −16 nm (i.e. the farther chosen positions of the three dimensional object on the lower side (e.g. the negative side) of the x-axis) to +21 nm (i.e. the farther chosen positions of the three dimensional object on the higher side (e.g. the positive side) of the x-axis), if the extent along the y-axis of the three-dimensional object is from −9 nm to +11 nm, and if the extent along the z-axis of the three-dimensional object is from −10 nm to +17 nm, then the extent of the cage could be for instance from −17 to 22 nm along the x-axis, from −10 to +12 nm along the y-axis and from −11 to +18 nm along the z-axis if a fixed value of 1 nm is chosen for the distance between the three-dimensional object and the cage. Another possibility is to consider that two out of three edges of the cuboid frame are correlated to each other, while the third edge is uncorelated. For instance, both edges could be kept at the same size or one could be kept twice as long as the other. Another possibility is to keep all three edges of the cuboid frame correlated to each other. One example is to keep all edges at the same size (the cuboid would here be a cube). Preferably, all edges are kept independent of each others. Preferably and independently of the shape of the cage selected, the dimensions of the cage are varied in order to minimise the distance between the cage and the three-dimensional object, more preferably, the dimensions of the cage are selected so that at least two positions on the object are not farther away, i.e. are closer, than 1 nm to the cage, most preferably 0.3 nm to the cage.

The fourth step consists in the calculation of the interaction between the three-dimensional object (e.g. the molecular species) and the cage. This will here be illustrated for a molecular species. The interaction between the molecular species and the enclosing cage can be estimated using standard equations well known to those in the art. One such equation is that of a typical coulombic interaction energy (Equation 5):

$$IE = \sum_{b=1}^{nAtoms} \sum_{c=1}^{nPoints} \frac{f(v_b)g(v_c)}{h(d_{bc})} \quad \text{(Equation 5)}$$

with IE the interaction energy for a particular property between a given molecular species and a given cage, nAtoms the total number of atoms in the given molecular species, nPoints the total number of points to which a property is assigned in the given cage, $v_b$ the value of the property at the b'th atom, $v_c$ the value of the property at the c'th cage point, and $d_{bc}$ the distance between atom b and cage point c. Functions f( ), g( ), and h( ) are mathematical transformation functions well known to those in the art. For instance, f(x)=x, g(x)=x, and h(x)=x. Transformations such as h(x)=x+k or h(x)=x²+k can be used as well (with k being a constant). The interaction energy IE is a specific example of interaction value $V_i$ among others. To be more general, equation 5 can be re-written as follow:

$$V_i = \sum_{b=1}^{nCoordinates} \sum_{c=1}^{nPoints} \frac{f(v_b)g(v_c)}{h(d_{bc})},$$

wherein nCoordinates is the total number of coordinates in the given three dimensional object, nPoints the total number of points to which a property is assigned in the given cage, $v_b$ the value of the property at the b'th coordinate, $v_c$ the value of the property at the c'th cage point, and $d_{bc}$ the distance between coordinate b and cage point c.

Other equations to evaluate the interaction between molecular species and cage are possible, and their application depends on the results one wants to achieve. For example, it might sometimes be desirable to evaluate the field similarity as a measure for interaction between a molecular species and a cage. Field similarity calculations have for example been described by Vinter et al (1995, *J. Comput.-Aided Mol. Des.* 9, 297-307) and Mestres et al. (1997, *J. Mol. Graph. Model.* 15, 114-121).

It is also possible to normalise the property values $V_b$ of the chosen positions of the three-dimensional object (e.g. of the atoms) prior to the evaluation of the interaction. This can be done in a number of ways, including for example by normalisation towards zero mean and unit variance, or by normalisation using a scaling factor such as for example described by Cheeseright et al. in WO 2004/023349:

$$f_m = 1 + \sum_{b=1}^{nAtoms 31} \left( \frac{v_b/v_m}{1+(d_{bm}/\alpha)^2} \right) \quad \text{(Equation 6)}$$

with $f_m$ being the scale factor to normalise atom m, $v_b$ and $v_m$ the property values of positions (e.g. atoms) b and m, respectively, $d_{bm}$ the distance between positions (e.g. atoms) b and m, and $\alpha$ a scale factor.

For the calculation of the descriptors, it was opted to use the lowest possible interaction energy as an estimate for the interaction between the molecular species and cage for a given property. Other ways to estimate this interaction energy can be used such as but not limited to the highest interaction energy or an interaction energy averaged over all orientations and/or conformations among others. For the purpose of minimising the interaction value $V_i$, the relative orientation between enclosing cage and molecular species has to be sampled over the entire rotational space. This is achieved by performing a full systematic search of the rotational space of the molecular species in small angular steps over the x-, y-, and z-axis, while keeping the orientation of the cage fixed. Any value for the angular steps can be chosen such as 40 degrees or below, preferably 30 degrees or below and most preferably 20 degrees or below. The lower limit for the value of the angular step is only limited by the available time and the fastness of the computer used. This because the lower this limit, the longer the required computing time for a given computer.

Alternately, the molecular species can be fixed and the cage rotated. Alternative interaction energy optimisation methods, well known to those in the art, may also be used such as but not limited to Monte-Carlo optimisation, molecular dynamics, minimisation techniques such as Newton-Raphson or conjugate gradients and the likes.

Optionally, in the case of molecular species, in addition to sampling the entire rotation space, sampling of the conformational space of the molecular species may also be performed if required.

After every rotational step or conformational change, the sizes of the enclosing cages are adjusted to the new orientation or conformation of the molecular species. The entire process is showed in FIG. 5.

Figure 5:
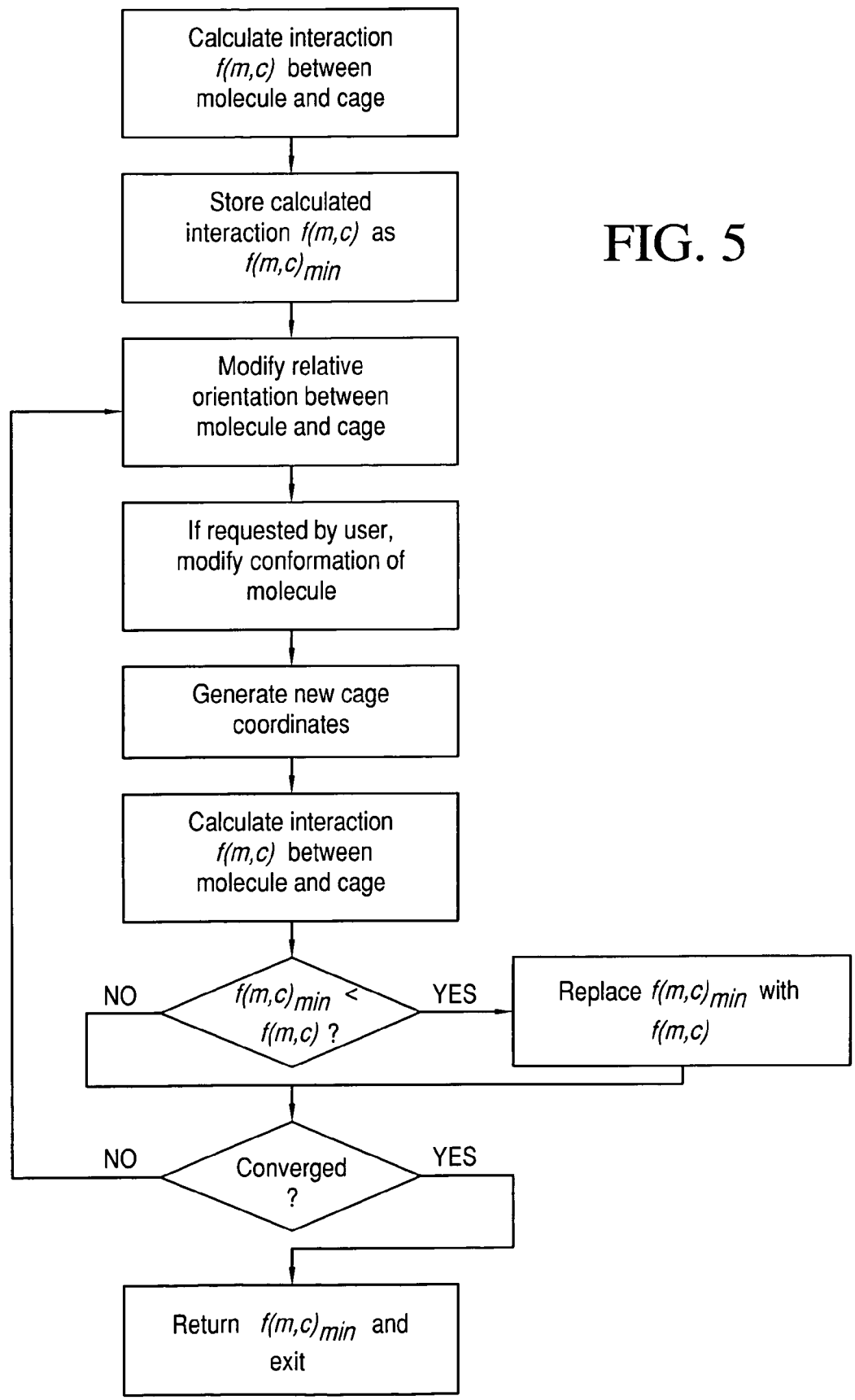
FIG. 5 is a flowchart showing the calculation of the interaction between a molecular species (e.g. a molecule) and its surrounding cage in an embodiment of the present invention.

According to an embodiment of the present invention as illustrated by FIG. 5, once the interaction f(m,c) between the molecular species (e.g. molecule) and the cage has been calculated, the next step consists in storing the calculated interaction f(m,c) as $f(m,c)_{min}$. Then, the next step consists in modifying the relative orientation between the molecular species (e.g. molecule) and the cage. The next step, which is an optional step, is to modify the conformation of the molecular species (e.g. molecule). The next step is to generate new cage coordinates. The next step is to calculated the interaction f(m,c) between the molecular species (e.g. molecule) in its new orientation relatively to the cage and/or its new conformation. If f(m,c) is smaller than $f(m,c)_{min}$, f(m,c) becomes the new $f(m,c)_{min}$. As long as no convergence is achieved for the value of $f(m,c)_{min}$, the process going from the modifying of the relative orientation between the molecular species (e.g. molecule) and the cage to the comparison between $f(m,c)_{min}$ with f(m,c) is repeated. Once a convergent value for $f(m,c)_{min}$ is obtained, $f(m,c)_{min}$ is saved and can be assigned to a position in the descriptor.

The next step consists in assigning each of the minimized interaction values Vi obtained to a distinct position in the string of interaction values forming the descriptor.

The last step consists in repeating the entire process for all other cages and for all other properties.

A single descriptor can comprise both $V_i$ and $V_v$ values. For instance, if all cages are cuboid cages, one $V_v$ value can be comprised in the descriptor. If cages of different shapes are used (e.g. of cuboid and ellipsoid shapes for instance), several $V_v$ values can be present in the descriptor in addition to the $V_i$ values.

FIG. 1 summarizes the general process by which descriptors are generated according to an embodiment of the present invention. In this embodiment, the three-dimensional shape of an object represented by a set of coordinates is the starting point of the process. The first step of the process consists in assigning a set of property values $V_b$ to each coordinates of the three-dimensional object.

The second step consists in the generation of the descriptor and the end point of the process is the generated descriptor itself.

Figure 2:
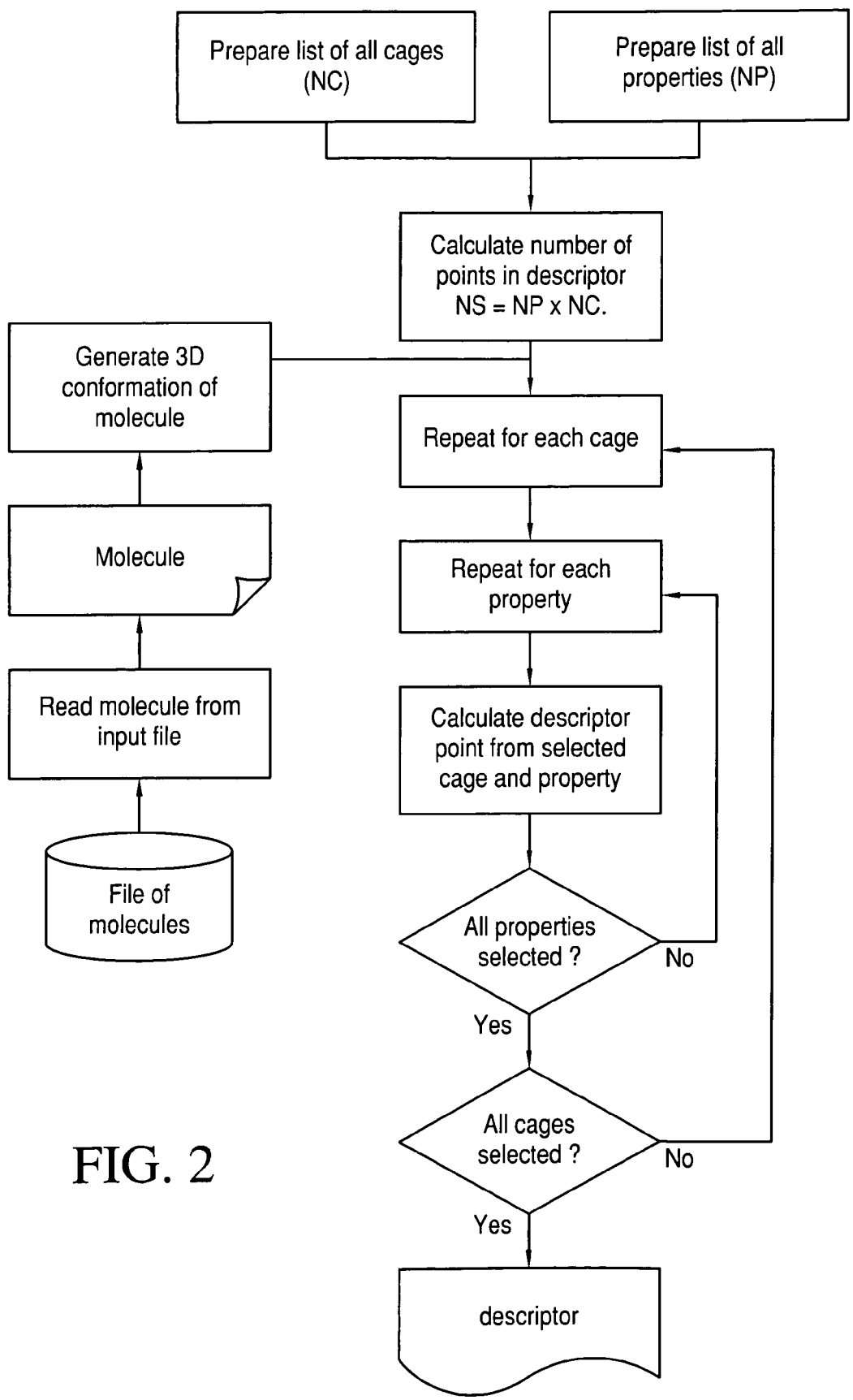
FIG. 2 is a flowchart showing a process of the generation of descriptors when applied to molecular species according to an embodiment of the present invention.

According to an embodiment of the present invention as illustrated by FIG. 2, the starting point of the method is a computer file containing molecular species (e.g. molecules). The first step of the method consist in reading a molecular species (e.g. a molecule) from the input file in order to extract this molecular species (e.g. molecule) from this file. The next step consists in generating the three-dimensional conformation of this molecular species (e.g. molecule). In parallel, a list of NC cages and a list of NP properties are prepared and the number of interaction values $V_i$ in the descriptor NS is calculated by multiplying NP by NC. In the next step, a first cage is selected. In the next step, a first property is selected. In the next step, a first interaction value of the descriptor is calculated from the first selected cage and the first selected property. If all properties of the list have not been selected yet for this cage, the next property on the list is selected and the next interaction value $V_i$ of the descriptor is calculated from the first selected cage and the second selected property. This process is repeated until all properties on the list have been selected and the corresponding interaction values $V_i$ of the descriptor calculated. If all cages of the list have not been selected yet, the next cage on the list is selected and the first property on the list is selected. In the next step, the next interaction values $V_i$ of the descriptor is calculated from the second selected cage and the first selected property. If all properties of the list have not been selected yet for this cage, the next property on the list is selected and the next interaction values $V_i$ of the descriptor is calculated from the second selected cage and the second selected property. This process is repeated until all properties on the list have been have been selected and the corresponding interaction values $V_i$ of the descriptor calculated. This process is repeated until all cages on the list have been selected and the corresponding interaction values $V_i$ of the descriptor calculated. The end point of this process is the resulting descriptor containing NS interaction values $V_i$.

Figure 3:
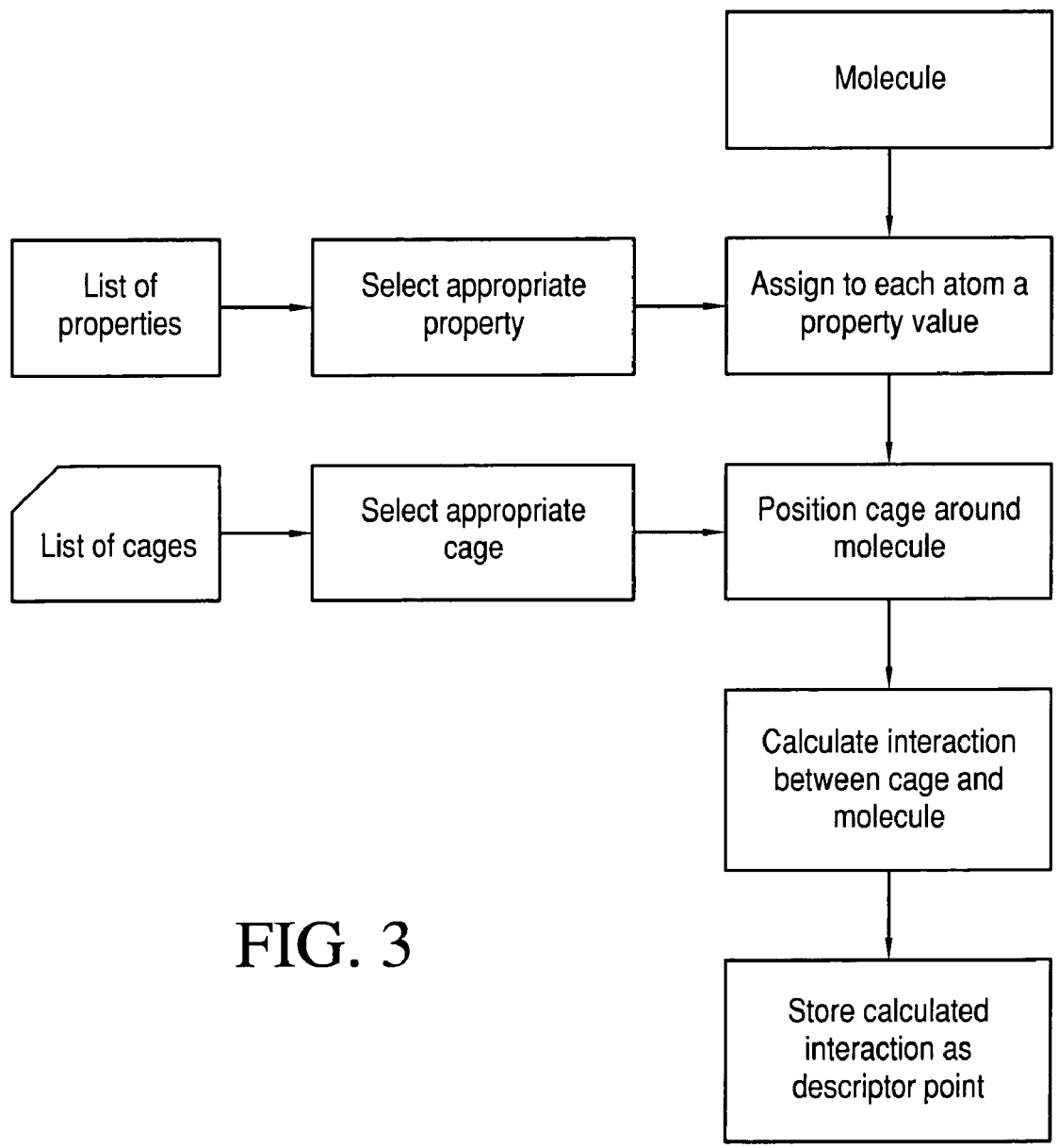
FIG. 3 is a flowchart showing the generation of a single descriptor interaction value $V_i$ (i.e. a descriptor point) when applied to molecular species according to an embodiment of the present invention.

According to an embodiment of the method illustrated by FIG. 3, the starting point of the method is a molecular species (e.g. a molecule), a list of properties and a list of cages. In a first step of the method, an appropriate property and an appropriate cage are selected from their corresponding lists. In the next step of the method, a property value of the selected appropriate property is assigned to each atom of the molecular species (e.g. molecule). In the next step, the selected appropriate cage is positioned around the molecular species (e.g. molecule). In the next step, the interaction between the cage and the molecular species (e.g. molecule) is calculated and in the final step of the method the calculated interaction is stored as an interaction values $V_i$ in the descriptor.

In another embodiment of the present invention, the descriptor of the three-dimensional object is generated by a computer-based method including the following steps:

When the three-dimensional object is a molecular species, the first step is to determine a three-dimensional configuration and a set of coordinates, i.e. a set of atomic positions for this molecular species via a computer simulation, one or more laboratory analysis means or via a combination of computer simulation and one or more laboratory analysis means. For instance, the molecular conformations can be generated by using programs such as but not limited to CORINA or Omega, derived experimentally by using methods such as but not limited to X-ray, infra-red spectroscopy (IR) or nuclear magnetic resonance (NMR) techniques or modelled according to a pharmacophoric pattern or hypothesis.

The second step consists in enclosing entirely the three-dimensional object (e.g. the molecular species) in a first cage of a set of one or more cages. The number of cages can be any number above or equal to one, preferably above or equal to four. These cages have a three-dimensional shape which can be any shape such as but not limited to polyhedra (such as but not limited to pyramids (e.g. tetrahedron), polygonal prisms (e.g. cuboids), polygonal antiprisms, and the likes), ellipsoids (e.g. sphere), cones, cylinders and the likes including truncated versions thereof. Each cage has a volume $V_v$. In this embodiment, the positioning of a set of points on the surface of the cages is optional and no properties are necessarily associated to the optional set of points on the surface of the cages. The positions and the orientation of the cage are generated in such a way that the cage encloses the three-dimensional object (e.g. the molecular species) entirely. In the example of a cuboid frame, a first possibility is to consider the x-, y-, and z-edges of the cuboid frame as being independent of each other, and as being defined by the x-, y-, and z-extents of the molecular species. Another possibility is to consider that two out of three edges of the cuboid frame are correlated to each other, while the third edge is uncorrelated. For instance, two edges could be kept at the same size or one of both could be kept twice as long as the other. Another possibility is to keep all three edges of the cuboid frame correlated to each other. One example is to keep all edges at the same size (the cuboid would here be a cube). Preferably, all edges are kept independent of each others. Preferably, the dimensions of the cage are varied in order to minimise the distance between the cage and the molecular species, more preferably, the dimensions and the position of the cage are selected so that at least two positions on the three-dimensional object are not farther away, i.e. are closer, than 1 nm to the cage, most preferably 0.3 nm to the cage. This way, the volume $V_v$ of the cage is minimised while keeping the three-dimensional object entirely enclosed in this cage.

The third step consists in assigning each of the minimised volume $V_v$ obtained to a distinct position in the string of interaction values forming the descriptor. The last step consists in repeating the entire process for all other cages. In another embodiment of the present invention, the descriptor can be generated from the active site of a protein, or any other pocket, of which the three-dimensional structure is available. This structure could be obtained by means of protein X-ray crystallography, NMR, or a theoretical approach. The hereby generated descriptors are named 'protein descriptors". These protein descriptors can be used to classify proteins according the physicochemical properties of their active sites, or to evaluate ligand binding by evaluating the similarity between the respective descriptors of both ligand and protein. Those descriptors are normally generated in four distinct steps:

1. Filling of the active site pocket with a set of cavity spheres;
2. Generation of a set of surface points around the set of cavity spheres;
3. Projection of the protein atomic properties onto the set of surface points;
4. Generation of a descriptor from the set of annotated surface points.

Sometimes it may be desirable to work via an intermediate step, in which the surface properties, as projected from the protein atoms, are fitted onto the set of spheres centers. This set is then used to generate a descriptor. The steps involved are in this case:

1. Filling of the active site pocket with a set of cavity spheres;
2. Generation of a set of surface points around the set of cavity spheres;
3. Projection of the protein atomic properties onto the set of surface points;
4. Reverse fitting of the properties on the surface points onto the set of cavity spheres;
5. Generation of a descriptor from the set of annotated cavity spheres.

The entire process is visually depicted in FIG. 7 and outlined below.

The first step relates to the filling of the active site pocket (4) with a set of cavity spheres (5).

Many algorithms have been described to fill a cavity (4) with a set of spheres (5). The algorithm as described by Laskowski (1995, *J. Mol. Graph.* 13, 323-330) can be implemented mutatis mutandis. In this procedure, each cavity sphere (5) is placed between a pair of protein atoms (6) midway between their van der Waals surfaces and just touching each. If any neighbouring protein atoms (6) penetrate this cavity sphere (5) its radius is reduced until it just touches the intruding atom (6). If the radius of the cavity sphere (5) falls below some predetermined minimum (for instance 1.5 Å), it is rejected. Otherwise, the sphere (5) is accepted and saved. When all pairs of protein atoms (6) have been considered the saved cavity spheres (5) fill the protein pocket. It is not always necessary to consider all atoms of the protein. It is sometimes sufficient to consider only 2-3 layers of protein atoms around the pocket.

Figure 7A:
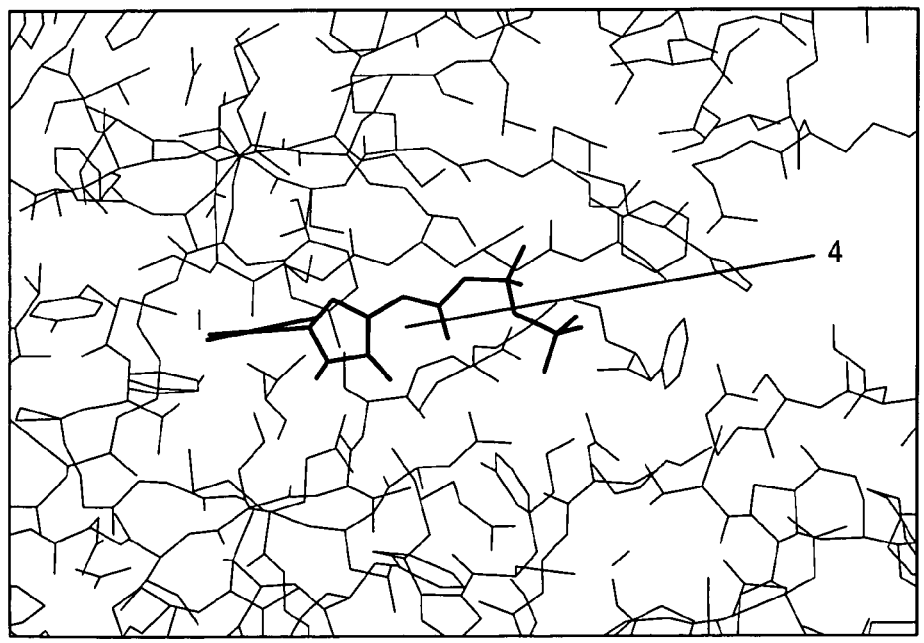
FIG. 7 illustrates the required steps to convert a protein pocket into a three-dimensional object from which a descriptor can be obtained according to an embodiment of the present invention.
Figure 7B:
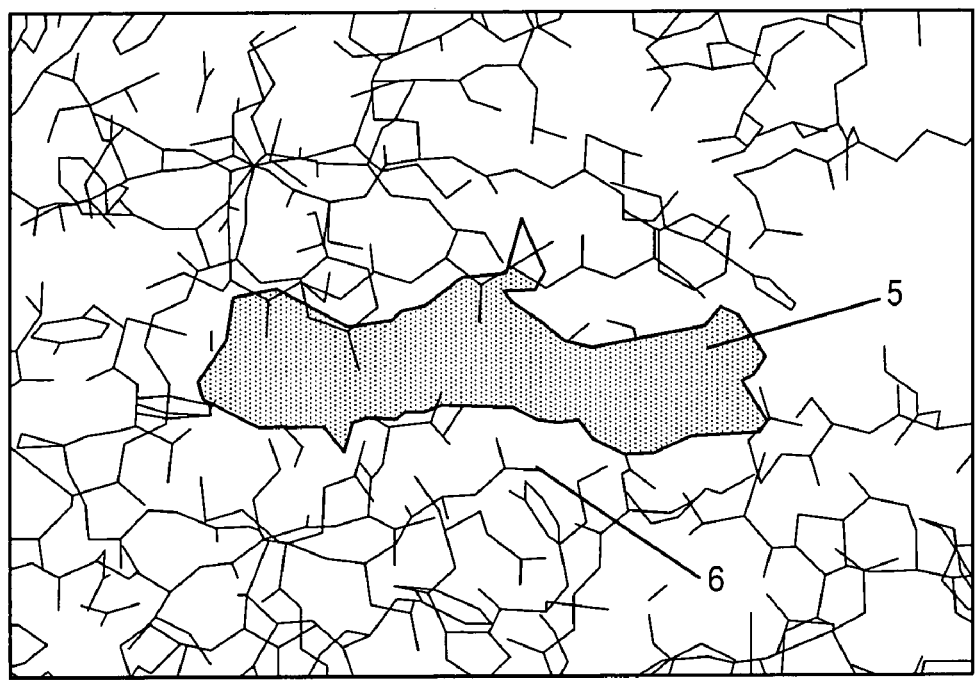

For a typical protein active site (4), such as the ATP-binding pocket of a protein kinase as shown in FIG. 7a, the here described sphere filling algorithm generates between 100 and 2000 sphere points (5) (FIG. 7b). In FIG. 7b, the sphere points are represented linked to neighbouring sphere points by lines. Those lines is a feature of the graphics program used and not a feature of the sphere filling algorithm. Each of these spheres (5) are described by the coordinates of the sphere centers and the corresponding sphere radii.

The second step relates to the generation of a set of surface points (7) around the set of cavity spheres (5).

From the set at hand of sphere points with corresponding radii, a surface is calculated that encompasses these sphere points. The surface resembles the van der Waals surface of the set of cavity spheres (5), except that crevices between the spheres (5) are smoothed over and interstices too small to accommodate the surface generation probe are eliminated. The required sphere center coordinates and radii are calculated in step 1, and surrounding protein atoms are excluded from the surface calculation. The molecular surface can for instance be calculated by the method described in Richards (1977, *Ann. Rev. Biophys. Bioeng.* 6, 151-176). According to Richards's definition, the molecular surface consists of two parts: contact surface and reentrant surface. The contact surface is made up of those parts of the van der Waals surface that can actually be in contact with the surface of the probe. The reentrant surface is defined by the interior-facing part of the probe when it is simultaneously in contact with more than one sphere point.

In the context of this invention, it was also found that an uniform density of surface points on the surface is critical to obtain a uniform protein property sampling in the subsequent steps 3 and 4. Surface point (7) densities for a typical surface encompassing a set of cavity sphere points (5) within a protein active site (4) can be equal or superior to 0.1 surface points (7) per squared Angstrom, preferably equal or superior to 0.5 surface points (7) per squared Angstrom. The higher limit for the surface point (7) density is only defined by the available time and the speed of the computer used. This because the higher this surface point (7) density, the longer the required computing time for a given computer.

Figure 7C:
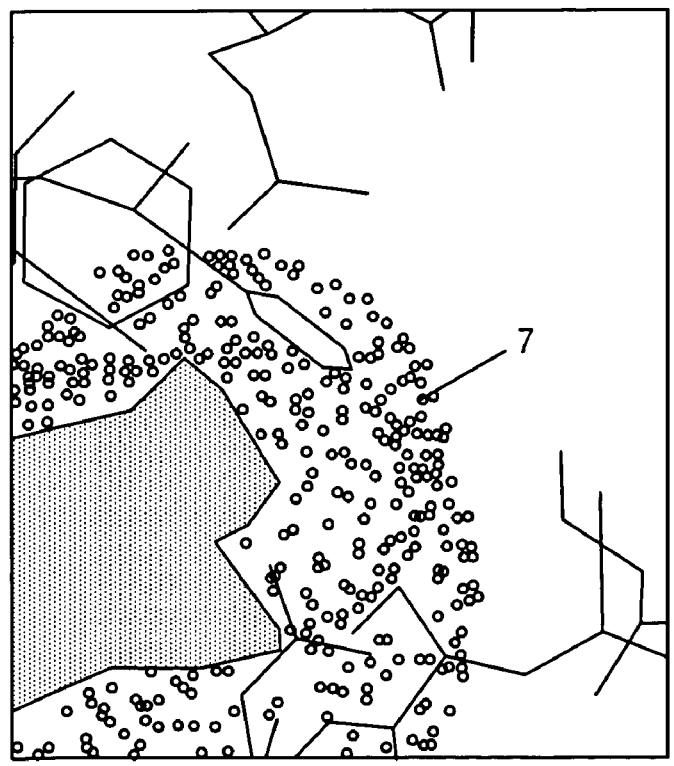

For a typical protein active site (4) such as the ATP-binding pocket of a protein kinase, the here described surface generation algorithm generates between 1000 and 5000 surface points (7) (FIG. 7c).

The third step relates to the projection of the protein atom properties onto the set of surface points (7).

In order to generate a descriptor from the set of surface points derived during step 2, each of the surface points (7) needs to be annotated with at least one or more property values. These property values are generated by projecting each of the different property values of the protein atoms onto each surface point (7), as can be done using the following equation:

$$v_p = \sum_{b=1}^{nAtoms} \frac{f(v_b)}{h(d_{b,p})} \qquad \text{(Equation 7)}$$

with $v_p$ the projected property value at surface point p, nAtoms the total number of atoms in the given protein, $v_b$ the value of the property at the b'th protein atom, and $d_{b,p}$ the distance between protein atom b and surface point p. Functions f( ) and h( ) are mathematical transformation functions well known to those in the art. For instance, f(x)=x or −x, and h(x)=x. Transformations such as h(x)=x+k or h(x)=x²+k can be used as well (with k being a constant). The here described procedure is repeated for each surface point (7), and for each property. Depending on the desired applications of the descriptors, a number of properties and transformation functions f(x) can be applied:

- If the purpose of descriptors is to compare and cluster a large series of protein active sites based on their physicochemical properties, it might be sufficient to use the well-known z-scales as property values (Sandberg et al., 1998, *J. Med. Chem.* 41, 2481-2491). In this case it is sufficient to assign, for example, each protein Cα atom the three z-scale values according the corresponding residue classification, and to transfer these atomic z-scale values onto each of the surface points (7) using equation 7. In this example, each of the surface points (7) will have three property values assigned (corresponding to the three z-scales).
- Alternatively, the protein descriptors obtained from protein pockets can also be compared with the descriptors of ligands (ligand descriptors). This might be performed in cases where one wants to evaluate the likelihood of ligand binding to a particular binding pocket, based on the assumption that high similarity between the descriptor of a protein pocket and the descriptor of a ligand is indicative of the complementarity between the protein pocket and the ligand. In these cases, it might often be necessary to guarantee that the properties which are used to generate both types of descriptors are fully compatible. In order to achieve this, it is both necessary that properties are used that can be calculated both for protein atoms as well as ligand atoms, and that appropriate transformation functions f(x) are applied to the protein properties. The purpose of these functions is to transform each of the property values of the protein atoms in a compatible format with the corresponding values of the ligand atoms. For instance, the following properties and transformation functions can be implemented:

| Property | Transformation function f(x) |
| --- | --- |
| Partial charges | x = −x |
| Lipophilicity | x = x |
| Softness | x = x |
| Hardness | x = x |
| Electrophilicity | x = x |

The final step in the generation of descriptors of protein pockets (protein descriptors) is to convert the surface points (7) with corresponding property values into a descriptor. This is achieved as previously described.

An Optional step is the reverse fitting of the properties on the surface points (7) onto the set of cavity spheres (5).

Once the protein properties have been projected onto the surface points (step 3), it is possible to fit the generated surface properties onto the interior sphere centers (5) before calculating a descriptor. Although not strictly required, it is nevertheless sometimes desirable to include this step since the protein descriptor which results from these annotated sphere center points will resemble more closely to a typical ligand descriptor (ligand descriptor) in terms of its absolute values.

This reverse fitting step can be implemented for instance following the method as described by Bayly et al. (1993, *J. Phys. Chem.* 97, 10269-10280) among others. According to this procedure, the properties of the cavity spheres (5) are calculated by fitting these properties to reproduce the properties of the surface points. A least-squares procedure is used to fit the property value $q_j$ to each sphere cavity j. The calculated potential at each of the surface points is given by:

$$\hat{v}_p = \sum_{j=1}^{nSpheres} \frac{q_j}{d_{pj}} \qquad \text{(Equation 8)}$$

so that the figure-of-merit $\chi^2$ to be minimized in the least-squares procedure is defined by:

$$\chi^2 = \sum_{p=1}^{nSurfacePoints} (v_p - \hat{v}_p)^2 \qquad \text{(Equation 9)}$$

Another embodiment of the present invention relates to a method of assessing the similarity between a reference three-dimensional object and a test three-dimensional object. The reference three-dimensional object can for instance be the binding pocket of a protein, a molecular species with known (biological or catalytic) activity (e.g. a molecular species with known affinity for a target protein or with known therapeutical effect) among others. The test three-dimensional objects are any objects that one would like to compare to the reference three-dimensional object. In the case of molecular species, those test three-dimensional objects can for instance be found in databases of existing or virtual molecular species. The aim of the screening of a databank is in general to find three-dimensional objects (e.g. molecular species) with similar activities (e.g. catalytic or biological activities) to that of the reference three-dimensional object. In order to assess the similarity between the reference three-dimensional object and the test three-dimensional object(s), the descriptors of both the reference and the test three-dimensional objects are calculated and compared as previously described. A descriptor based virtual high throughput screening is typically performed in five distinct steps:

1) generation of molecular conformations from the molecular species of a database;
2) generation of the descriptor corresponding to the molecular conformations generated in 1);
3) calculation of a reference descriptor;
4) similarity calculation between the reference descriptor and the test descriptors;
5) sorting the database and selection of database molecular species having a higher similarity with the reference descriptor.

Another embodiment of the present invention relates to a method of generating a three-dimensional quantitative structure activity relationship (3D-QSAR) of a series of molecular species. QSAR are mathematical relationships linking chemical structures represented in the form of descriptors and biological activity in a quantitative manner for a series of molecular species. The QSAR method of the present invention is three-dimensional because it makes use of descriptors derived from three-dimensional molecular representations of species.

The first step of the method consists in obtaining a three-dimensional configuration for each of the molecular species of the series. This can be done as previously described.

The second step of the method consists in generating a descriptor for each three-dimensional configuration. This can be done as previously described.

The third step of the method consists in associating each descriptor to a biological activity.

The fourth step of the method consists in defining a plurality of equations, each equation corresponding to one molecular species of the series, wherein in each equation, the measured biological activity of the corresponding molecular species is set equal to a weighted linear combination of said values. this weighted linear combination is weighted by unknown coefficients and the plurality of equations forms a system of equations.

The fifth step consist in finding an at least approximate solution to the system of equations. This solution is the set of coefficients coming the closest to make each equation true.

Figure 11:
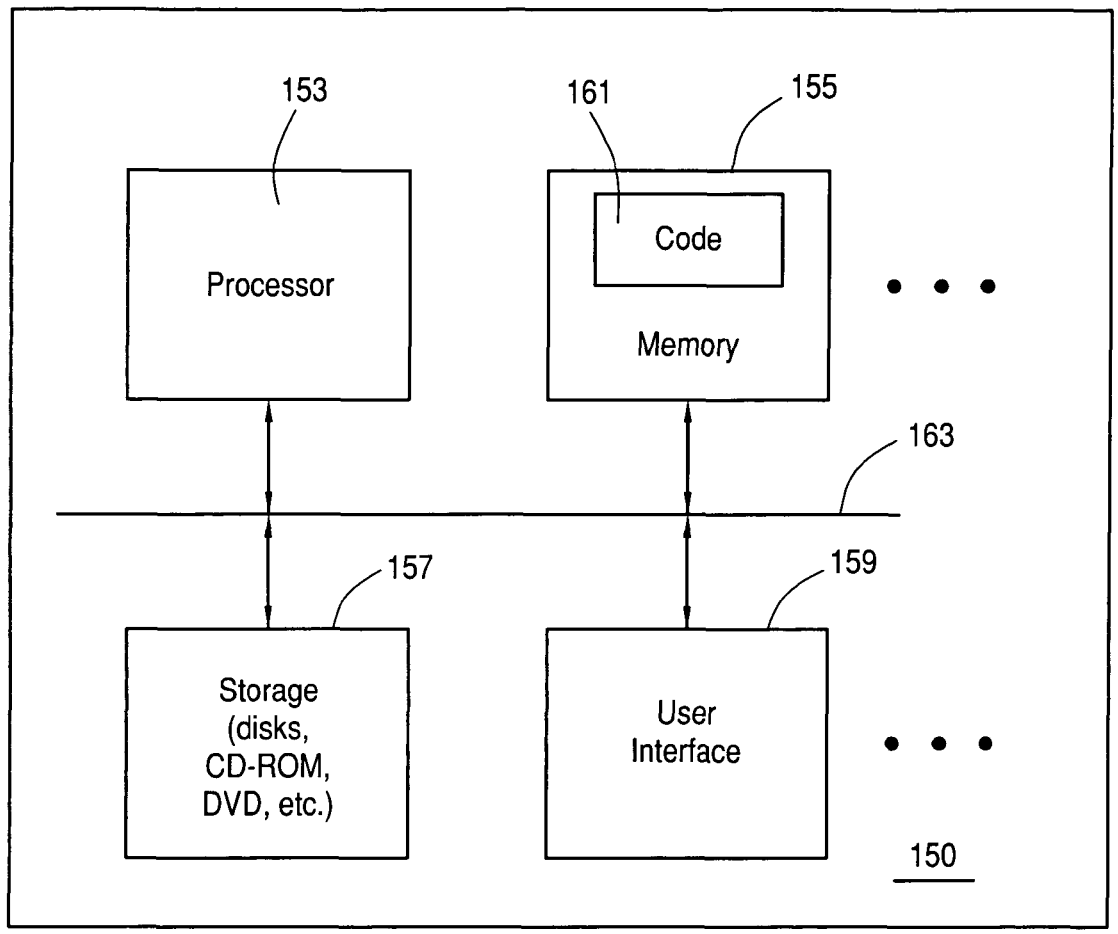
FIG. 11 is an example of a computer system that may be used with the present invention.

Such method embodiments as are described above may be implemented in a processing system 150 such as shown in FIG. 11. FIG. 11 shows one configuration of processing system 150 that includes at least one programmable processor 153 coupled to a memory subsystem 155 that includes at least one form of memory, e.g., RAM, ROM, and so forth. A storage subsystem 157 may be included that has at least one disk drive and/or CD-ROM drive and/or DVD drive. In some implementations, a display system, a keyboard, and a pointing device may be included as part of a user interface subsystem 159 to provide for a user to manually input information. Ports for inputting and outputting data also may be included. More elements such as network connections, interfaces to various devices, and so forth, may be included, but are not illustrated in FIG. 11. The various elements of the processing system 150 may be coupled in various ways, including via a bus subsystem 163 shown in FIG. 11 for simplicity as a single bus, but will be understood to those in the art to include a system of at least one bus. The memory of the memory subsystem 155 may at some time hold part or all (in either case shown as 161) of a set of instructions that when executed on the processing system 150 implement the step(s) of any of the method embodiments described herein. Thus, while a processing system 150 such as shown in FIG. 11 is prior art, a system that includes the instructions to implement novel aspects of the present invention is not prior art, and therefore FIG. 11 is not labelled as prior art.

It is to be noted that the processor 153 or processors may be a general purpose, or a special purpose processor, and may be for inclusion in a device, e.g., a chip that has other components that perform other functions, for example it may be an embedded processor. Also with developments such devices may be replaced by any other suitable processing engine, e.g. an FPGA. Thus, one or more aspects of the present invention can be implemented in digital electronic circuitry, or in computer hardware, firmware, software, or in combinations of them. Furthermore, aspects of the invention can be implemented in a computer program product tangibly embodied in a carrier medium carrying machine-readable code for execution by a programmable processor. Method steps of aspects of the invention may be performed by a programmable processor executing instructions to perform functions of those aspects of the invention, e.g., by operating on input data and generating output data.

Furthermore, aspects of the invention can be implemented in a computer program product tangibly embodied in a carrier medium carrying machine-readable code for execution by a programmable processor. The term "carrier medium" refers to any medium that participates in providing instructions to a processor for execution. Such a medium may take many forms, including but not limited to, non-volatile media, and transmission media. Non-volatile media includes, for example, optical or magnetic disks, such as a storage device which is part of mass storage. Volatile media includes mass storage. Volatile media includes dynamic memory such as RAM. Common forms of computer readable media include, for example a floppy disk, a flexible disk, a hard disk, magnetic tape, or any other magnetic medium, a CD-ROM, any other optical medium, punch cards, paper tapes, any other physical medium with patterns of holes, a RAM, a PROM, an EPROM, a FLASH-EPROM, any other memory chip or cartridge, a carrier wave as described hereafter, or any other medium from which a computer can read. Various forms of computer readable media may be involved in carrying one or more sequences of one or more instructions to a processor for execution. For example, the instructions may initially be carried on a magnetic disk of a remote computer. The remote computer can load the instructions into its dynamic memory and send the instructions over a telephone line using a modem. A modem local to the computer system can receive the data on the telephone line and use an infrared transmitter to convert the data to an infrared signal. An infrared detector coupled to a bus can receive the data carried in the infrared signal and place the data on the bus. The bus carries data to main memory, from which a processor retrieves and executes the instructions. The instructions received by main memory may optionally be stored on a storage device either before or after execution by a processor. The instructions can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

EXAMPLE 1

In this example, the protein descriptor of the active site of a cAMP-dependent protein kinase in complex with MNAMP-PNP (PDB-code: 1CDK), using z-scales as protein properties and with dodecapoles as interaction cages, has been calculated and looks as follows:

(1177.0235104, 1241.9454472, 5309.7227832, 7739.9044175, 3592.9170204, 3663.1235402, 3318.7667805, 5557.9750177, 4513.2625606, 4810.0268823, 4637.8198335, 7039.2447879, 3817.8125232, 2729.4127530, 8871.0996326, 7871.9820890, 4041.8094676, 2803.1417433, 2658.5126972, 8796.1666293, 7880.8818501, 5062.2250856, 4396.6414940, 8478.5168524, 1093.6344578, 571.7572775, 869.4288781, 2070.4729018, 2584.8578515, 2290.0349962, 1641.3678263, 1685.1768608, 1948.6745828, 3197.5941913, 3538.7587911, 2291.4695265)

This descriptor is generated from the three z-scale property values in combination with twelve non-stereospecific dodecapole cages, resulting in a total of 36 data points (12 cages times 3 properties).

The descriptor for the same cAMP-dependent protein kinase, however now in complex with MNATP (PDB-code: 1ATP), is:

(1451.0615659, 1452.3946320, 4791.0736889, 6525.2927839, 4491.6511286, 3202.0090141, 2376.0092687, 4881.4240683, 5349.9589960, 4515.2041767, 5586.4489508, 5915.8262652, 4405.5709945, 3078.4106003, 8424.1878645, 8998.8770307, 5154.5239871, 4336.7009250, 3026.1709973, 8173.1688876, 8747.2194043, 6645.3295798, 6430.0893508, 6598.1402542, 904.00873950, 548.4988372, 694.4875240, 2051.4446135, 2530.8606115, 2320.2737774, 1939.2617181, 2157.2011781, 2093.2625232, 3375.3180364, 3552.9222586 2349.7615051)

On the other hand, the generated descriptor for the ATP-binding pocket of a different protein kinase, the CDK2 protein kinase in complex with purvanalol B (PDB-code: 1CKP), differentiate itself clearly from the descriptors of the two cAMP-dependent kinases:

(2382.6536642, 1474.7309051, 2092.6384519, 4267.5679973, 6382.3308870, 5523.3496559, 4150.7807419, 3018.0932592, 4312.2598303, 6536.9238770, 7715.0819416, 4417.0939360, 2061.3033873, 1464.6906777, 3633.7372348, 5459.4372702, 6556.4724403, 4929.9911477, 4520.3761649, 5945.4945549, 6251.8003512, 7558.1630982 8220.1978131, 7044.5718066, 504.9865912, 300.1583540, 537.9934145, 802.0223370, 1176.5070111, 1174.3539725, 1059.1203880, 1120.4337701, 1124.4183724, 1451.3004884, 1687.0289938, 1102.4849312)

Figure 8:
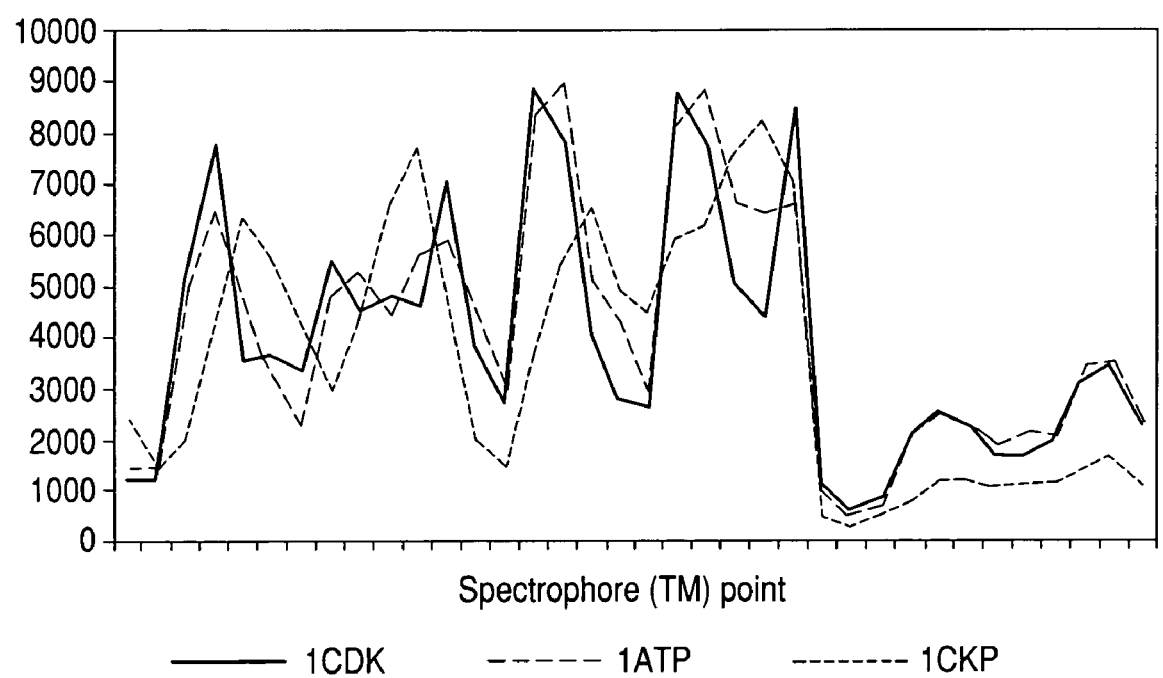
FIG. 8 illustrates the representation of three examples of descriptors according to a specific example of the present invention.

The three descriptors are graphically compared in FIG. 8. FIG. 8 shows the similarities between the respective descriptors of 1CDK and 1ATP and the differences between those two descriptors and the descriptor corresponding to 1CKP.

1 CDK and 1ATP are both cAMP-dependent protein kinases, but with different inhibitors bound to their active sites, while 1CKP is the protein kinase CDK2.

EXAMPLE 2

The here described example of virtual screening is based on research as published by McElroy and coworkers in 2003 (*J. Med. Chem.* 46, 1066-1080). In this work, the inhibition of human and murine soluble epoxide hydrolase by a large series of urea-like molecular species has been described. For the purpose of this example, ten molecular species, all with $IC_{50}$ values less or equal than 0.2 μM, were randomly selected from the publication and were subsequently divided in two sets:

The 'actives' set. Three out of the ten molecular species were labelled as being the 'confirmed active' molecular species. These molecular species were randomly chosen from the ten selected molecular species, and were used to calculate a single reference descriptor with associated weight factors. This reference descriptor with its associated weight factors was used to search a molecular database for molecular species having similar activities.

The database of 'unknowns'. The remaining seven molecular species were inserted in a subset of the Maybridge molecular database containing 993 drug-like molecular species of which the pharmacological activity with respect to epoxide hydrolase inhibition was unknown. The resulting database consisted therefore of in total 1000 molecular species, of which at least seven molecular species had an $IC_{50}$ value less or equal than 0.2 μM for the inhibition of human soluble epoxide hydrolase.

The chemical structures and inhibition constants of the ten molecular species are shown in the table below:

| ID | Structure | $IC_{50}$ (μm) | Set |
|---|---|---|---|
| 122 | 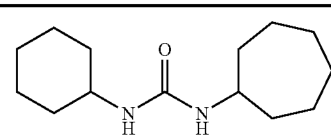 | 0.10 | 'Confirmed active' |
| 125 | 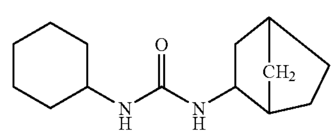 [SMILES: O=C(NC1CCCCC1)NC1CC2CCC1C2] | 0.10 | 'Confirmed active' |
| 127 | 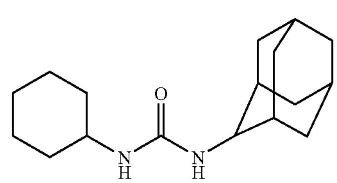 [SMILES: O=C(NC1CCCCC1)NC1C2CC3CC(C2)CC1C3] | 0.10 | 'Confirmed active' |
| 136 | 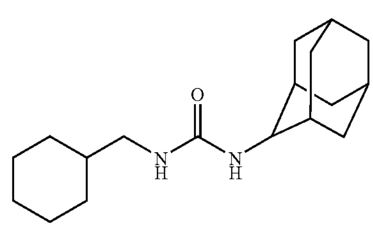 [SMILES: O=C(NCC1CCCCC1)NC1C2CC3CC(C2)CC1C3] | 0.10 | 'Unknown active' |

-continued

| ID | Structure | IC$_{50}$ (μm) | Set |
|---|---|---|---|
| 141 | 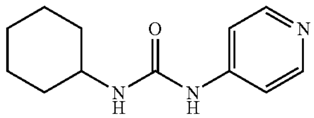 [SMILES: O=C(Nc1ccncc1)NC1CCCCC1] | 0.15 | 'Unknown active' |
| 143 | 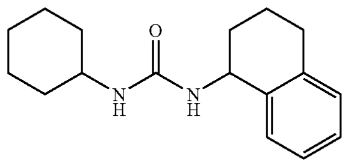 [SMILES: O=C(NC1CCCCC1)NC1CCCc2ccccc21] | 0.10 | 'Unknown active' |
| 149 | 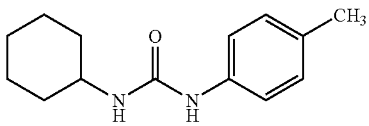 [SMILES: Cc1ccc(NC(=O)NC2CCCCC2)cc1] | 0.17 | 'Unknown active' |
| 153 | 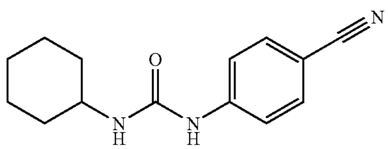 [SMILES: N#Cc1ccc(NC(=O)NC2CCCCC2)cc1] | 0.10 | 'Unknown active' |
| 155 | 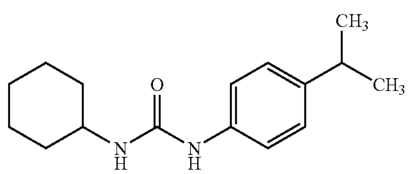 [SMILES: CC(C)c1ccc(NC(=O)NC2CCCCC2)cc1] | 0.07 | 'Unknown active' |
| 163 | 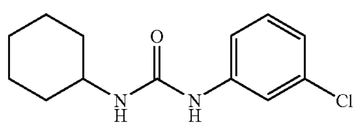 [SMILES: O=C(Nc1cccc(Cl)c1)NC1CCCCC1] | 0.19 | 'Unknown active' |

The purpose of this example is to demonstrate the applicability of the descriptors according to the present invention with respect to the selection from databases of molecular species with well-defined pharmacological properties. Prior to the generation of descriptors, molecular conformations need to be calculated. For this purpose, conformations were calculated for each molecular species using the OMEGA program of OpenEye Scientific Software. This resulted in a single three-dimensional conformation for each molecular species. Descriptors were calculated for all the molecular species (the three molecular species of the 'confirmed actives' set, and the 1000 database molecular species). The following atomic properties were used to calculate the descriptors:

Shape index,
Partial atomic charges, using the EEM-approximation (Bultinck et al., 2002, *J. Phys. Chem. A.* 106, 7895-7901);
Atomic electrophilicities, using the EEM-approximation;
Atomic softness, using the EEM-approximation;
Atomic lipophilicities, as described by Gaillard et al., 1994, *J. Comput. Aided Mol. Des.* 8, 83-96.

Twelve non-stereospecific dodecapole cages were used for the calculation of the interaction values $V_i$, which resulted for each molecular species in a descriptor consisting of 60 interaction values $V_i$ [12 (number of cages) by 5 (number of properties)]. For example, the descriptor of molecular species 122 in the table hereabove is given:

(1.6493547, 2.4467502, 3.0259994, 3.1405621, 2.6612200, 2.2822862, 1.7679167, 3.4061206, 3.0566774, 2.8076934, 2.6721218, 3.6771842, 1.3812835, 2.4409513, 3.3207675, 2.9868924, 1.4800005, 1.5467830, 0.4984696, 3.3188026, 3.2676320, 1.3759867, 0.9193736, 2.2404641, 9.3956598, 15.5909196, 9.5878893, 8.9463201, 9.9863238, 11.1901966, 3.5517550, 9.4718922, 10.8558505, 10.2552206, 6.7633472, 11.8095674, 31.6654207, 51.7477946, 63.6184823, 72.0496439, 41.9713097, 47.7432800, 18.1939267, 60.4060183, 41.2523642, 40.5303563, 38.2618646, 77.0991979, 18.3943909, 32.5058646, 44.2222734, 39.7760980, 19.7089946, 20.5983293, 6.6380618, 44.1961070, 43.5146740, 18.3238541, 12.2431910, 29.8359995)

Next, a reference descriptor has been calculated by taking the weighed average of the three individual descriptors of molecular species 122, 125, and 127 (the 'actives' set). This resulted in the following reference descriptor:

(1.6499500, 2.4562700, 3.0806100, 3.2749400, 3.3286100, 2.5996200, 2.1886500, 3.6824700, 3.4585900, 3.1786300, 3.2799000, 3.5231800, 1.3174300, 2.3967500, 3.1889000, 3.0633700, 1.4048900, 1.5853000, 0.4906850, 3.3675900, 3.3374600, 1.6244800, 1.0346100, 2.1837400, 9.2680200, 16.2342000, 10.0758000, 9.4229200, 10.7091000, 14.7422000, 5.7789300, 13.2777000, 13.8001000, 13.7852000, 11.4665000, 12.1918000, 30.5559000, 51.4414000, 61.0996000, 78.3450000, 39.8737000, 54.7513000, 24.0170000, 59.6234000, 45.8535000, 51.1712000, 47.4466000, 80.5812000, 17.4780000, 31.8035000, 42.2614000, 40.5944000, 18.6294000, 21.0721000, 6.5280600, 44.6714000, 44.2680000, 21.5703000, 13.7544000, 28.9717000)

Calculation of the weighed average can be achieved in a number of ways. However, in the present example, the weights were taken as being the statistical F-ratios from the set of the three 'actives', on the one hand, and the molecular species within the 'unknowns' database, on the other hand. Using the statistical F-ratios as weight factors has the advantage that differences in both means and variances are taken into account. In this example, the derived weight factors were:

(1.8908700, 0.9900330, 0.5853290, 1.3174900, 1.5539800, 1.8989600, 1.7088700, 1.1945000, 1.6524800, 1.9966900, 1.6752200, 1.7104300, 1.1428600, 0.2739840, 0.9337710, 1.1269600, 2.1171600, 1.6434200, 2.5066000, 1.1415000, 0.9121310, 2.4198700, 2.6895400, 2.2596800, 0.0181191, 0.5348470, 0.8856620, 1.5213600, 1.1831100, 0.4052540, 1.5956600, 1.4294900, 1.3199900, 1.2416200, 1.6402600, 1.5015700, 0.0375171, 0.1986550, 0.1295690, 0.3360140, 0.0091109 0.1698740, 0.0228813, 0.0635029, 0.0019022, 0.0030144, 0.0076395, 0.2657470, 0.0151632, 1.0090400, 0.1722870, 0.0423767, 0.7984770, 0.0820521, 1.9608100, 0.0701633, 0.3405390, 0.9287420, 2.1138600, 0.6018120)

Next, using the reference descriptor with its associated weight factors, and the database of 1000 molecular species of unknown activity, similarities could be calculated between the reference descriptor and each of the 1000 descriptor within the database. The similarities were obtained by calculating the normalised distance between each pair of descriptors:

$$d = \sqrt{\frac{\sum_{i=1}^{n}(s_i - r_i)^2 w_i}{\sum_{i=1}^{n} s_i^2 w_i + \sum_{i=1}^{n} r_i^2 w_i}}$$ (Equation 10)

with d being the normalised distance, n the number of descriptor interaction values (in this example 60), $s_i$ the i'th point of the database descriptor, $r_i$ the i'th point of the reference descriptor, and $w_i$ the i'th weight factor. A large similarity is indicated by a small d, and vice versa.

Figure 6:
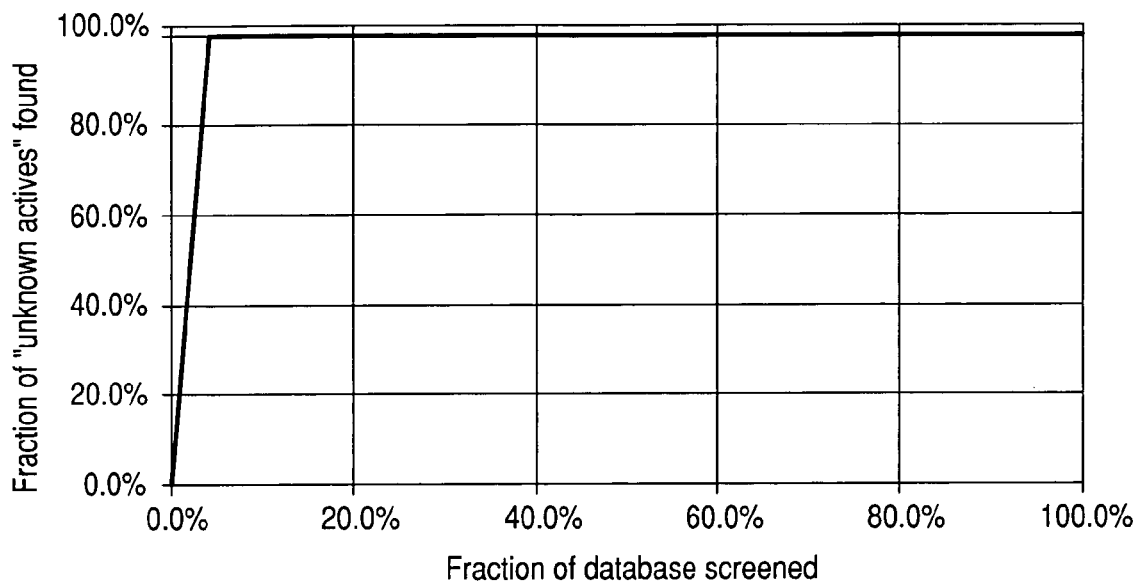
FIG. 6 shows an enrichment plot of a high-throughput screening test performed using descriptors according to an embodiment of the present invention.

The last step consisted in the selection of molecular species from the database for which the calculated descriptor have a large similarity with the reference descriptor. In the context of this example, the sorted database had the seven molecular species with an $IC_{50} \leq 0.2$ μm located within its top 4%. This means that these seven molecular species, having an $IC_{50} \leq 0.2$ μm for sHE inhibition, were all located within the top 40 of the sorted database of 1000 molecular species, or in a non-virtual world, it should have been sufficient to biochemicaly test only the top-4% of the entire ranked database to identify at least seven other molecular species having the desired sHE inhibitory activity. This is visually depicted in FIG. 6. In FIG. 6, the x-axis refers to the fraction of the ranked database screened and the y-axis referred to the fraction of active molecular species founded. It shows an enrichment plot of sHE virtual high-throughput screening and it demonstrates that the seven active molecular species where all located within the top-4% of a ranked database translated to a 25-fold database enrichment.

EXAMPLE 3

As an example of the application of descriptors for the generation of quantitative structure-activity relationships, the development of a blood-brain penetration model is given here. Accurate predictions of passive drug blood-brain barrier penetration, expressed as steady-state distribution profiles, are of great interest and value to the pharmaceutical industry, and as consequence a great deal of computational models have been described in the literature during the recent years. In the context of this example, a model of passive blood-brain barrier (BBB) penetration is described using the descriptors of the present invention in combination with two optimisation models. In the context of this example, both a Generalized Linear Model (GLM) and a Support Vector Machine (SVM) have been used as optimization algorithms, although other choices, such as neural networks among others, are also possible. Experimental data were obtained from the paper by Rose and coworkers (2002, *J. Chem. Inf. Comput. Sci.* 42, 651-666) describing more than 100 BBB distributions in combination with structural information. Sixty-six randomly chosen data points were used as a training set, and 33 data points were kept separate as an internal test data set. External validation of the model was performed using the 57 data points as described by Clark (1999).

The first two steps consist in the generation of molecular conformations and descriptors.

For each of the in total 156 molecular species, a single conformation was generated using Omega (OpenEye Scientific Software, USA). Five atomic properties were used to calculate the descriptors:

Shape index;
Partial atomic charges, using the EEM-approximation;
Atomic electrophilicities, using the EEM-approximation;
Atomic softness, using the EEM-approximation;
Atomic lipophilicities, as described by Gaillard et al.

Five non-stereospecific and one stereospecific octapole cages were used for the calculation of the interaction values, which resulted for each molecular species in a descriptor consisting of 30 interaction values (6 values per property times 5 properties).

Figure 9A:
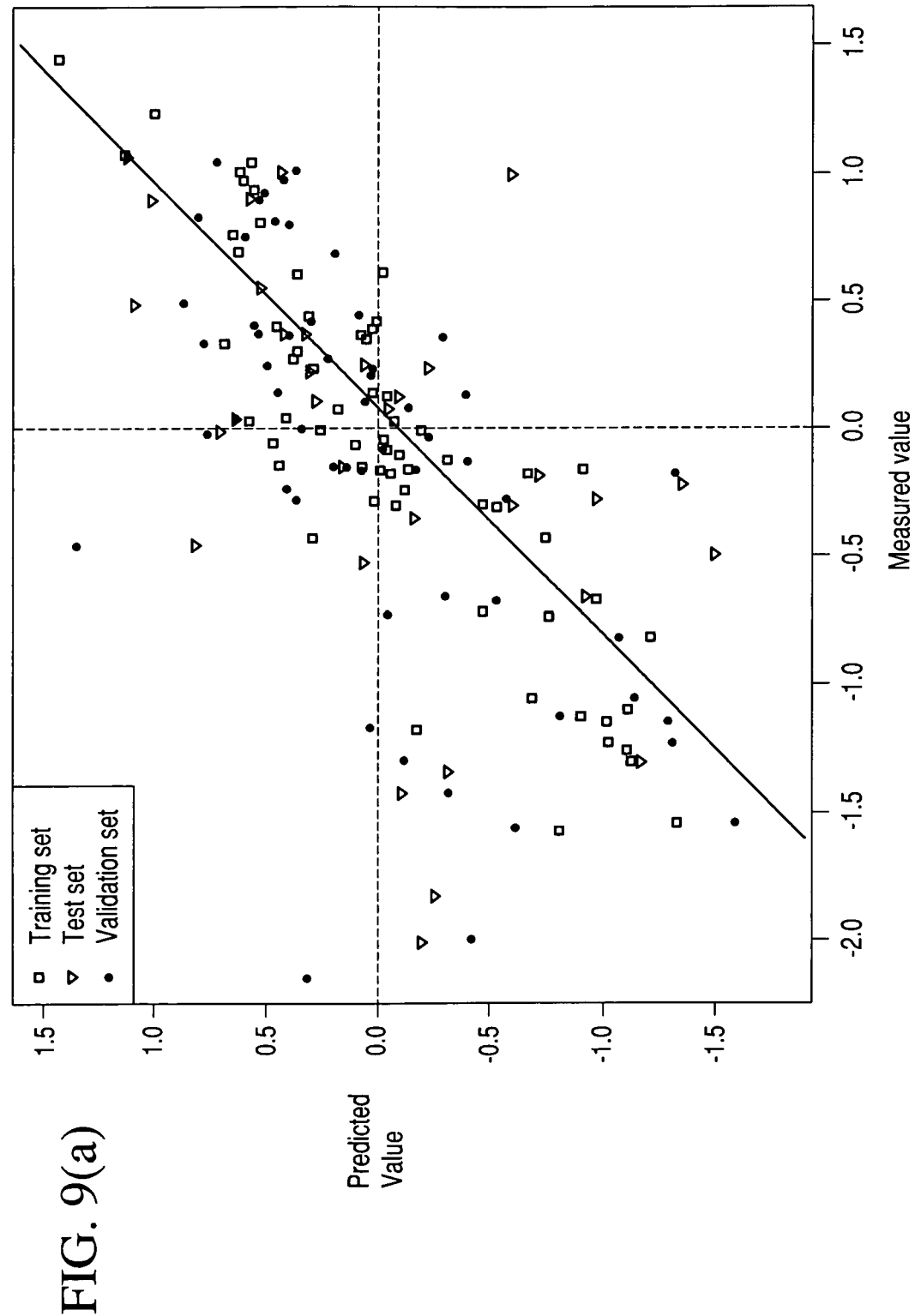
FIG. 9 illustrates the results of a three-dimensional quantitative structure-activity relationship (3D-QSAR) performed on descriptors according to an embodiment of the present invention.
Figure 9B:
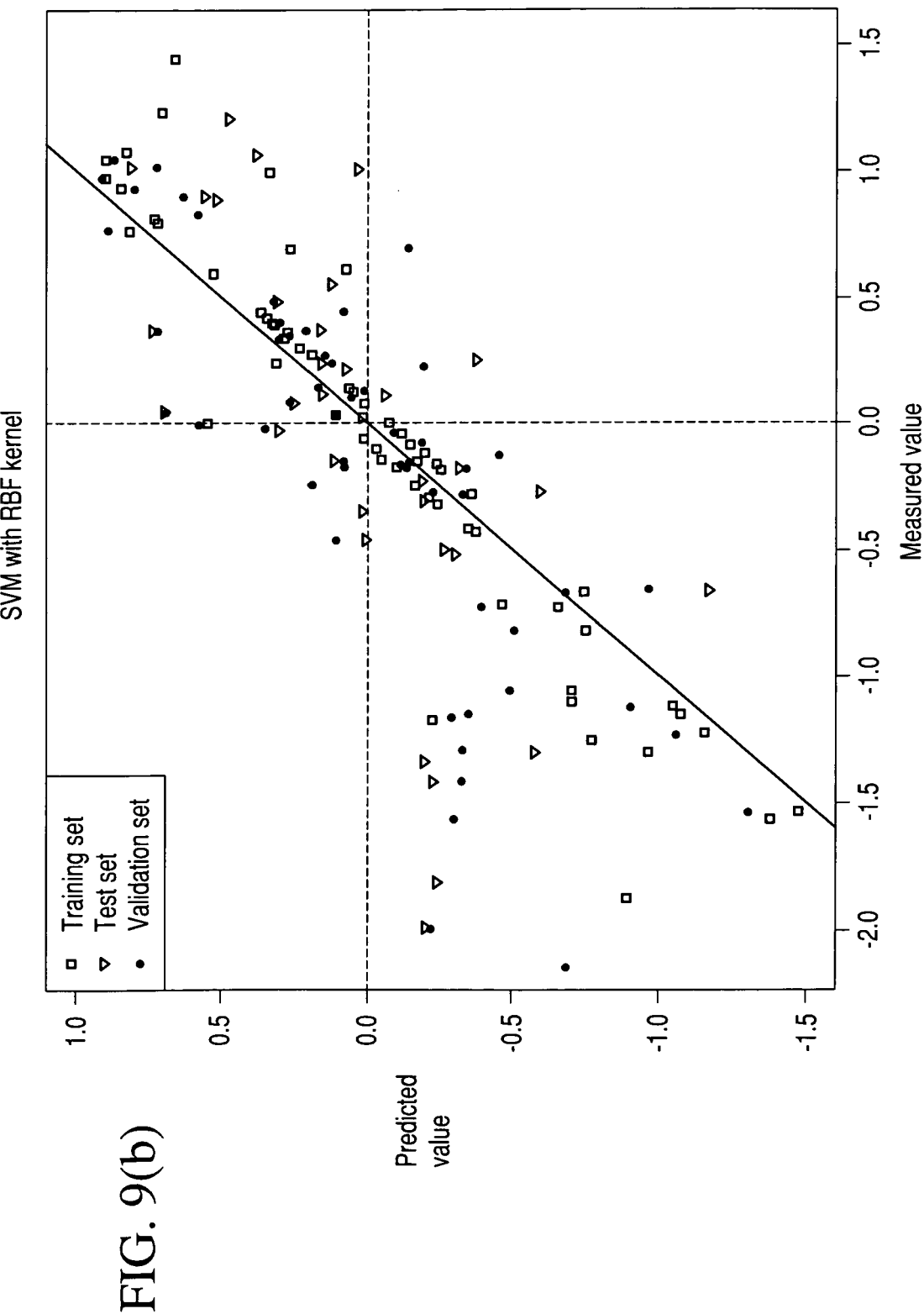

The third step consist in the calculation and validation of a QSAR model. Although several kernels were evaluated for the SVM optimisation, a Radial Basis Function (RBF) kernel was selected as the best choice based on the obtained results for the internal test set consisting of 33 molecular species. The resulting models from the GLM and the SVM optimisation are presented in FIGS. 9(a) and 9(b) respectively. In FIGS. 9(a) and 9(b), the abscise and ordinate labels are in log-units of the relative brain/blood concentrations. White squares are the training set; white triangles are the test set and black points are the validation set. The respective mean-squared errors (MSE) were 0.57 for the GLM and 0.41 log-units for the SVM for the internal test set. For the external validation set, the respective mean-squared errors (MSE) were 0.44 for the GLM and 0.25 log-units for the SVM. For the external validation dataset, of the 28 molecular species experimentally determined to penetrate the blood-brain barrier, 26 molecular species are predicted correctly. Alternatively, of the 29 brain-impermeable molecular species, 24 are predicted correctly.

Figure 10:
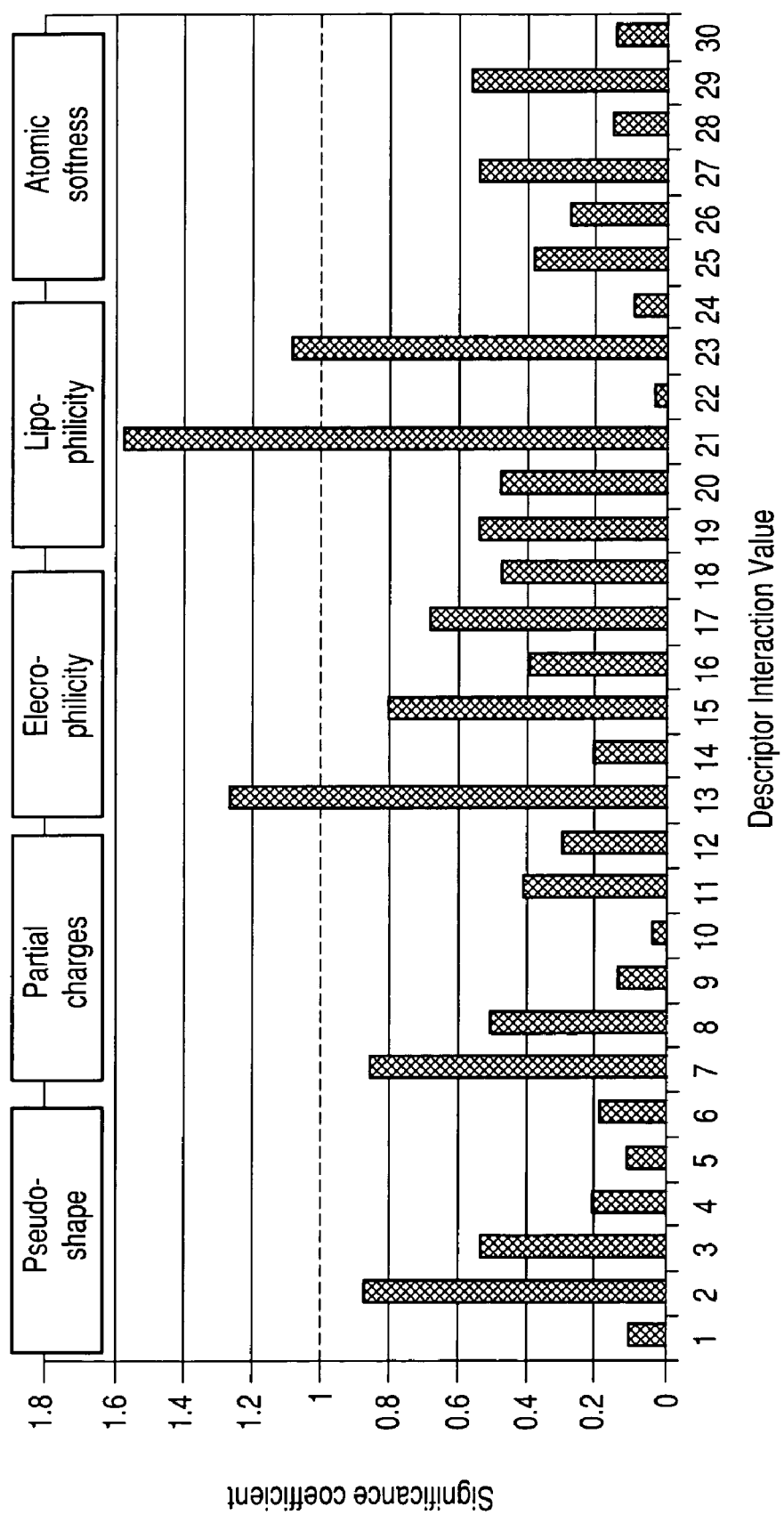
FIG. 10 illustrates the result of a three-dimensional quantitative structure-activity relationship (3D-QSAR) performed on descriptors according to an embodiment of the present invention.

Significance levels for the 30 parameters according the GLM model are shown in FIG. 10. FIG. 10 shows the significance of each of the 30 descriptor interaction values $V_i$ with respect to blood-brain barrier penetration modelling. Electrophilicity and lipophilicity are the most significant parameters for the correlation of structures with penetration data. Both electrophilicity and lipophilicity seem to be the most significant parameters for the correlation of molecular structures with BBB-penetration data, which is consistent with the widely-accepted thought that lipophilicity plays a major role in the transport of drugs throughout the blood-brain barrier.

The invention claimed is:

1. A method of generating a descriptor, said descriptor being a string of interaction values $V_i$ of a three-dimensional object represented by a set of coordinates, and said object having one or more properties at chosen coordinates, each property represented by a value Vb, said method comprising the steps of:
   (i). determining a three-dimensional configuration of the object, including said set of coordinates, by using a computing device to perform a computer simulation of the object, by using means for performing a laboratory analysis of the object, or by using a combination of said computing device for performing a computer simulation of the object and said means for performing a laboratory analysis of the object,
   (ii). enclosing entirely said three-dimensional object in a cage of a set of one or more cages, each said cage having one or more interaction points, each said interaction point having one or more properties represented by value Vc,
   (iii). for each property and for each cage of said set of one or more cages, while keeping said three-dimensional object entirely enclosed in said cage by varying one or more dimensions of said cage, minimizing the interaction value $V_i$ for said property resulting from the interaction between said property at said chosen coordinates of said three dimensional object and said property at said interaction points of said cage by changing the relative orientation between the three-dimensional object and said cage, and
   (iv). assigning each of the obtained minimized interaction values $V_i$ to a distinct position in said descriptor.

2. A method according to claim 1, wherein said value $V_c$ is either +1, 0 or −1.

3. A method according to claim 2, wherein said value $V_c$ is either +1 or −1.

4. A method according to any of claims 1, wherein the sum of the values $V_c$ for each cage is zero.

5. A method according to claim 1, wherein for the minimizing of the interaction value $V_i$, the dimensions of the cage are selected so that at least two positions on the object are closer than 1 nm to the cage.

6. A method according to claim 1, wherein said set of points comprises between four and twelve points.

7. A method according to claim 1, wherein at least one of said cages is stereospecific.

8. A method according to claim 1, wherein said one or more cages are selected from cuboid cages on the surface of which said set of points are:
   a) four points occupying half of the corners of each face of said cuboid cage, or
   b) six points occupying the center of each face of said cuboid cage, or
   c) eight points occupying all corners of said cuboid cage, or
   d) twelve points occupying the middle of each edge of said cuboid cage.

9. A method according to claim 1, wherein said one or more cages are four or more cages.

10. A method according to claim 1, wherein each value $V_b$ is normalized before to perform step (iii).

11. A method according to claim 1, wherein at least one of said one or more cages is a cuboid.

12. A method according to claim 1, wherein said three-dimensional object is a three-dimensional configuration of a molecular species and wherein said chosen coordinates are chosen atomic positions.

13. A method according to claim 12, wherein said chosen atomic positions are all the atomic positions of said three-dimensional configuration of said molecular species.

14. A method according to any of claims 12, further comprising the step of optimizing the conformation of said three-dimensional configuration of said molecular species after step (ii) and before step (iv) so as to minimize the calculated interaction value $V_i$ resulting from the interaction between said three-dimensional configuration of said molecular species and said cage or so as to minimize the volume $V_v$ of said cage while keeping said three-dimensional object entirely enclosed in said cage.

15. A method according to claim 1, wherein said three-dimensional object is a surface obtained from a biomolecule pocket by a method comprising the steps of:
   a) filling said biomolecule pocket with a set of one or more spheres and
   b) generating a surface around said set of one or more spheres.

16. A computer program product stored on a non-transitory computer-readable data carrier, comprising software code for implementing method of generating a descriptor, said descriptor being a string of interaction values $V_i$ of a three-dimensional object represented by a set of coordinates, said object having one or more properties at chosen coordinates, each property represented by a value Vb, said method comprising performing the steps of:
   enclosing entirely said three-dimensional object in a cage of a set of one or more cages, each said cage having one or more interaction points, each said interaction point having one or more properties represented by a value Vc,
   (ii) for each property and for each cage of said set of one or more cages, while keeping said three-dimensional object entirely enclosed in said cage by varying one or more dimensions of said cage, minimizing the interaction value $V_i$ for said property resulting from the interaction between said property at said chosen coordinates of said three dimensional object and said property at said interaction points of said cage by changing the relative orientation between the three-dimensional object and said cage, and
   (iii) assigning each of the obtained minimized interaction values $V_i$ to a distinct position in said descriptor,
when executed on a computing system.

17. A non-transitory machine readable data carrier storing a computer program comprising software code for implementing a method of generating a descriptor, said descriptor being a string of interaction values $V_i$ of a three-dimensional object represented by a set of coordinates, said object having one or more properties at chosen coordinates, each property represented by a value Vb, said method comprising performing the steps of:
   (iv) enclosing entirely said three-dimensional object in a cage of a set of one or more cages, each said cage having one or more interaction points, each said interaction point having one or more properties represented by a value Vc,
   (v) for each property and for each cage of said set of one or more cages, while keeping said three-dimensional object entirely enclosed in said cage by varying one or more dimensions of said cage, minimizing the interaction value $V_i$ for said property resulting from the interaction between said property at said chosen coordinates of said three dimensional object and said property at said interaction points of said cage by changing the relative orientation between the three-dimensional object and said cage, and (vi) assigning each of the obtained minimized interaction values $V_i$ to a distinct position in said descriptor, when executed on a computing system.

* * * * *